US010045942B2

(12) United States Patent
Nakayama et al.

(10) Patent No.: US 10,045,942 B2
(45) Date of Patent: Aug. 14, 2018

(54) POROUS METAL OXIDE PARTICLES, PRODUCTION METHOD THEREOF AND APPLICATION THEREOF

(71) Applicant: MITSUI CHEMICALS, INC., Tokyo (JP)

(72) Inventors: Norio Nakayama, Chiba (JP); Hongbo Wang, Singapore (SG); Haruyuki Makio, Singapore (SG)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/892,385

(22) PCT Filed: May 14, 2014

(86) PCT No.: PCT/JP2014/062812
§ 371 (c)(1),
(2) Date: Nov. 19, 2015

(87) PCT Pub. No.: WO2014/188924
PCT Pub. Date: Nov. 27, 2014

(65) Prior Publication Data
US 2016/0089334 A1 Mar. 31, 2016

(30) Foreign Application Priority Data

May 22, 2013 (JP) ................. 2013-107963
Oct. 11, 2013 (JP) ................. 2013-213548

(51) Int. Cl.
*A61K 9/14* (2006.01)
*C01B 33/12* (2006.01)
(Continued)

(52) U.S. Cl.
CPC ............ *A61K 9/14* (2013.01); *C01B 13/32* (2013.01); *C01B 33/12* (2013.01); *C01B 37/02* (2013.01);
(Continued)

(58) Field of Classification Search
None
See application file for complete search history.

(56) References Cited

U.S. PATENT DOCUMENTS

2004/0035751 A1  2/2004  Plee
2009/0286070 A1  11/2009 Kumazawa
(Continued)

FOREIGN PATENT DOCUMENTS

EP  1479651 A1  11/2004
JP  2003335506 A2  11/2003
(Continued)

OTHER PUBLICATIONS

Okubo et al, JP 2008-280193, English Machine Translation from PAJ website.*
International Search Report dated Aug. 19, 2014 filed in PCT/JP2014/062812.
Jie Fan et al: "Low-Temperature Strategy to Synthesize Highly Ordered Mesoporous Silicas with Very Large Pores", Journal of American Chemical Society, 2005, 127, pp. 10794-10795.
Extended European Search Report dated Dec. 15, 2016 issued in the corresponding European patent application No. 14801195.0.

*Primary Examiner* — Colin W Slifka
(74) *Attorney, Agent, or Firm* — Rankin, Hill & Clark LLP

(57) ABSTRACT

Provided are porous metal oxide particles, in which 50% mean particle size by volume is equal to or larger than 50 nm and equal to or smaller than 300 nm, ratio of 90% mean particle size by volume to 50% mean particle size by volume (D90/D50) is equal to or lower than 2.0, the particles have mesopores having a pore size determined by BJH method of equal to or larger than 5 nm and equal to or smaller than 30 nm, and the structure of the pores is a three-dimensional cubic phase structure.

22 Claims, 9 Drawing Sheets

(51) Int. Cl.
  *C08K 7/26*   (2006.01)
  *F16L 59/02*  (2006.01)
  *C09D 11/00*  (2014.01)
  *C09D 201/00* (2006.01)
  *C08K 7/24*   (2006.01)
  *C08L 101/00* (2006.01)
  *C01B 37/02*  (2006.01)
  *C01B 13/32*  (2006.01)
  *C09D 11/037* (2014.01)
  *C09D 7/40*   (2018.01)

(52) U.S. Cl.
  CPC .......... *C08K 7/24* (2013.01); *C08K 7/26* (2013.01); *C08L 101/00* (2013.01); *C09D 7/40* (2018.01); *C09D 11/00* (2013.01); *C09D 11/037* (2013.01); *C09D 201/00* (2013.01); *F16L 59/028* (2013.01); *C01P 2004/04* (2013.01); *C01P 2004/32* (2013.01); *C01P 2004/45* (2013.01); *C01P 2004/52* (2013.01); *C01P 2004/62* (2013.01); *C01P 2004/64* (2013.01); *C01P 2006/12* (2013.01); *C01P 2006/16* (2013.01); *C01P 2006/17* (2013.01)

(56) References Cited

U.S. PATENT DOCUMENTS

| | | |
|---|---|---|
| 2011/0318249 A1 | 12/2011 | Nagai |
| 2012/0111231 A1 | 5/2012 | Maruguchi |
| 2012/0171936 A1* | 7/2012 | Haerle .............. B24B 37/044 |
| | | 451/59 |
| 2015/0259512 A1 | 9/2015 | Hirai |

FOREIGN PATENT DOCUMENTS

| | | |
|---|---|---|
| JP | 2004525846 | 8/2004 |
| JP | 2005263550 A2 | 9/2005 |
| JP | 2008165040 A2 | 7/2008 |
| JP | 2008280193 A2 | 11/2008 |
| JP | 2009091211 A2 | 4/2009 |
| JP | 2012-233148 | 11/2012 |
| WO | 2007060884 A1 | 5/2007 |
| WO | 2010103856 A1 | 9/2010 |

* cited by examiner (a)

BJH PORE SIZE ($r_p$: RADIUS) OBTAINED BY BJH METHOD FROM
ISOTHERMAL LINE IN ADSORPTION SIDE OF NITROGEN ADSORPTION (b)

COMMUNICATING PORES ($r_p$: RADIUS) BETWEEN MESOPORES
PRESENTED BY BJH METHOD FROM ISOTHERMAL LINE IN
DESORPTION SIDE OF NITROGEN ADSORPTION

POROUS METAL OXIDE PARTICLES, PRODUCTION METHOD THEREOF AND APPLICATION THEREOF

FIELD OF THE INVENTION

The present invention relates to porous metal oxide particles, a method of producing porous metal oxide particles and an application thereof.

BACKGROUND

In recent years, porous metal oxide materials are expected as materials that can be newly applicable to optical materials, low-dielectric constant materials, thermal insulation materials, medicines (DDS: drug delivery system), molecular probes, catalysts, adsorbent materials, sensors, paints, inks and the like. For example, it is thought that good insulation effect is obtained by adding in the resin film or paint a porous material having air layers therein as a filler, or in particular adding a porous material having pore that is smaller than mean free path of air in atmospheric pressure, namely smaller than 68 nm, for the purpose of improvement of thermal insulation performance.

Patent Document 1 describes a method of producing porous metal oxide particles using micelles of a surfactant as a template, and also describes that porous metal oxide particles having particle size of 20 to 200 nm, containing mesopores having pore size of 1 to 10 nm are obtained.

Patent Document 2 describes a method for synthesizing a mesoporous metal oxide having three-dimensional cubic phase structure using micelles of a surfactant as a template, and also describes that a mesoporous metal oxide having mean pore size of 5 nm is obtained (Example 2 and FIG. 6).

Patent Document 3 describes a method of producing a porous metal oxide material by using water-insoluble polymer particles, and also describes that a porous metal oxide material, in which mesopores form cubic phase and the pore size is substantially uniform within the range of from 5 to 30 nm, is obtained. Further, this also describes an example of producing porous particles having particle size of from 1 to 10 μm by spray-dry process (Example a12 and the like).

In addition, the following applications are considered.

An image display surface of an image display device such as a liquid crystal display, a CRT display, a projection display, a plasma display, an electroluminescence display, a reflection screen and the like is required to have scratch resistance, so as to avoid damage at the time of handling.

In such situation, a general practice is that a hard coating film is installed on a display surface of the image display device to improve the scratch resistance thereof.

The hard coating layer is formed by using a hard coating material, which is cured by an activation energy derived from ultraviolet, electron beam and the like or by heat, and such hard coating material is generally composed of binder components and fine inorganic particles having higher hardness (see Patent Document 4).

In addition, it is required to reduce reflection of light caused by an external light source such as fluorescent lamp and the like for the above described displays and the like, in order to enhance the visibility of the display surface. A possible approach to reduce the reflection of the extraneous light is an adjustment of the refractive index of the hard coating layer. Simply, the refractive index of the hard coating layer is lowered as compared with the refractive index of the display surface of the image display device. Alternatively, an approach for lowering the refractive index of the surface part of the hard coating layer as compared with that of the hard coat layer may be used. Alternatively, there may be another approach, which is providing coat layers from the side of the hard coating layer, the former having higher refractive index and the latter having lower refractive index of which thickness and refractive index are suitably adjusted on the basis of optical calculations in relation to the refractive index of the hard coating layer.

One can think of a method of using a fluorine-based coating material having low refractive index as a method for reducing the refractive index of the hard coating layer, however, such method is not satisfactory in terms of the curability. One can also think of a method of adding inorganic particles having lower refractive index into a binder component as another approach. Examples of the inorganic particles having low refractive index include silica particles and particles of fluoride such as magnesium fluoride, lithium fluoride, aluminum fluoride, calcium fluoride, sodium fluoride and the like; however, since the refractive index of silica is about 1.44, which is not very low, the effect of adding thereof is small. Although the fluoride particles provide low refractive index, it is difficult to stably obtain fine particles having small particle size. Patent Document 5 describes a method of using hollow silica particles as the inorganic particles having low refractive index. By having air layers that have a low refractive index inside the particles, hollow silica particles achieve a low refractive index as particles. Patent Document 6 describes a method of producing hollow silica particles by utilizing calcium carbonate as a template.

RELATED DOCUMENTS

Patent Documents

[Patent Document 1]
Japanese Laid-Open Patent Publication No. 2008-280193
[Patent Document 2]
Japanese Laid-Open Patent Publication No. 2003-335506
[Patent Document 3]
WO 2010/103856 pamphlet
[Patent Document 4]
Japanese Laid-Open Patent Publication No. 2008-165040
[Patent Document 5]
WO 2007/060884 pamphlet
[Patent Document 6]
Japanese Laid-Open Patent Publication No. 2005-263550

SUMMARY OF THE INVENTION

Problem to be Solved by the Invention

However, the technologies described in the above Patent Documents 1 to 3 have problems as described below. The method of Patent Document 1 is unsuitable for adsorption and incorporation of functional molecule having relatively larger molecular size, since the mesopore size of the obtained porous metal oxide (silica) particle is up to 10 nm at a maximum. Also, a proportion of mesopores in one particle cannot be freely changed, and thus it is difficult to change respective characteristics such as optical characteristic, dielectric constant characteristics, heat insulating characteristics and the like. Further, since the porous metal oxide particles have mesopores of cylindrical (hexagonal) structure, thicknesses of walls between the respective mesopores are thinner as a whole, in comparison with that of three-dimensional cubic phase structure, leading to insufficient mechanical strength. This possibly results in collapse of the mesopore structure in the use thereof for the paints and the like. Further, when the particle sizes of the porous metal oxide particles are larger and the particle sizes are not homogeneous, or more specifically for example, when such type of particles having mean particle size equal to or larger than 100 nm (0.1 µm) are mixed in a resin, the resultant product easily becomes opaque, and thus is not preferable for optical applications.

The method of Patent Document 2 is also unsuitable for the adsorption and the incorporation of functional molecules having relatively larger molecular size similarly as in the Patent Document 1, and further, since a proportion of mesopores in one particle cannot be freely changed in the method, it is difficult to change the respective characteristics such as optical characteristic, dielectric constant characteristics, heat insulating characteristics and the like. In addition to all the above, Patent Document 2 does not describe any methods for producing particles composed of a porous metal oxide material.

While Patent Document 3 describes porous metal oxide particles, in which mesopores create cubic phase and the pore size is substantially homogeneous within the range of from 5 to 30 nm, it does not describe particles having a smaller mean particle size and being homogeneous in particle size. Also, hollow particles obtained by a method of Patent Document 6 utilize calcium carbonate as a template, and thus it is considered that controls of the particle size and the hollow structure inside the particle are difficult.

Therefore, it is desirable to develop porous metal oxide particles and to establish a manufacturing method of those particles, in which the particles have mesopores equal to or larger than 5 nm in size and the pore structure thereof is an ordered three-dimensional cubic phase structure and further in which the mean particle size is smaller than that of the conventional particles and the particle sizes are homogeneous. However, a sufficiently satisfactory production method has not yet been developed.

Solution to Problem

The present invention is made in view of the problems described above, and is to provide porous metal oxide particles and a method of producing thereof, in which a mean particle size of the particles is in a range equal to or larger than 50 nm and equal to or smaller than 300 nm and the particle sizes are homogeneous, and in which the particles have mesopores with pore sizes equal to or larger than 5 nm and equal to or smaller than 30 nm, and pore structure thereof is an ordered three-dimensional cubic phase structure.

More specifically, the present invention can be described as follows.

[1] Porous metal oxide particles,
the 50% mean particle size by volume thereof being equal to or larger than 50 nm and equal to or smaller than 300 nm,
the ratio of 90% mean particle size by volume to 50% mean particle size by volume (D90/D50) being equal to or lower than 2.0,
the particles having mesopores having a pore size determined by BJH method equal to or larger than 5 nm and equal to or smaller than 30 nm, and
the structure of the pores being a three-dimensional cubic phase structure.

[2] The porous metal oxide particles as described in [1],
wherein the 50% mean particle size by volume thereof is equal to or larger than 50 nm and equal to or smaller than 100 nm,
the ratio of 90% mean particle size by volume to 50% mean particle size by volume (D90/D50) is equal to or lower than 1.5,
the particles have mesopores having a pore size determined by BJH method equal to or larger than 5 nm and equal to or smaller than 30 nm, and
the structure of the pores is a three-dimensional cubic phase structure.

[3] A method of producing the porous metal oxide particles as described in [1] or [2], comprising:
a step of obtaining a mixture comprising water and/or an organic solvent miscible or partially miscible with water, water-insoluble polymer particles having 50% mean particle size by volume equal to or larger than 5 nm and equal to or smaller than 30 nm, and a base catalyst;
a step of obtaining organic and inorganic composite particles by mixing a metal oxide precursor to the aforementioned mixture and carrying out a sol-gel reaction of the metal oxide precursor; and
a step of removing the water-insoluble polymer particles from the organic and inorganic composite particles.

[4] The method of producing the porous metal oxide particles as described in [3],
wherein the water-insoluble polymer particles are particles composed of a terminal branched polyolefin based copolymer represented by the following general formula (1), and having number average molecular weight equal to or lower than $2.5 \times 10^4$.

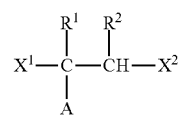

(In the formula, A represents polyolefin chain. $R^1$ and $R^2$ represent hydrogen atom or alkyl group having 1 to 18 carbon atoms and at least one thereof is hydrogen atom. $X^1$ and $X^2$, which may be the same or different groups, represent a group having straight or branched polyalkylene glycol group.)

[5] The method of producing the porous metal oxide particles as described in [4],
wherein $X^1$ and $X^2$ of the terminal branched polyolefin based copolymer represented by the general formula (1) are the same or different groups, and are represented by general formula (2)

(In the formula, E represents oxygen atom or sulfur atom, $X^3$ represents polyalkylene glycol group or group represented by general formula (3):

(In the formula, $R^3$ represents m+1 valent hydrocarbon group. G, which is the same or different groups, represents a group represented by $—OX^4$ or $—NX^5X^6$ ($X^4$ to $X^6$ represent a polyalkylene glycol group.). m represents a number of bonds of $R^3$ with G and is an integer of from 1 to 10.))
or are represented by general formula (4).

(In the formula, $X^7$ and $X^8$, which are the same or different groups, represent a polyalkylene glycol group or group represented by the above-described general formula (3).)

[6] The method of producing the porous metal oxide particles as described in [4] or [5],
wherein the terminal branched polyolefin based copolymer is represented by the following general formula (1a) or general formula (1b).

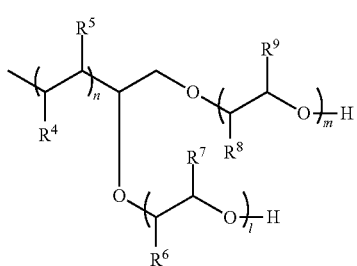

(1a)

(In the formula, $R^4$ and $R^5$ represent hydrogen atom or alkyl group having 1 to 18 carbon atoms and at least one thereof is hydrogen atom. $R^6$ and $R^7$ represent hydrogen atom or methyl group wherein at least one thereof is hydrogen atom, $R^8$ and $R^9$ represent hydrogen atom or methyl group and at least one thereof is hydrogen atom. l+m represents an integers equal to or larger than 2 and equal to or smaller than 450. n represents an integer equal to or larger than 20 and equal to or smaller than 300.)

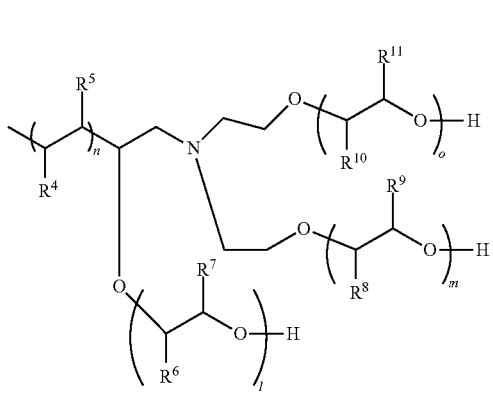

(1b)

(In the formula, $R^4$ and $R^5$ represent hydrogen atom or alkyl group having 1 to 18 carbon atoms and at least one thereof is hydrogen atom. $R^6$ and $R^7$ represent hydrogen atom or methyl group and at least one thereof is hydrogen atom, $R^8$ and $R^9$ represent hydrogen atom or methyl group and at least one thereof is hydrogen atom, $R^{10}$ and $R^{11}$ represent hydrogen atom or methyl group and at least one thereof is hydrogen atom. l+m+o represents an integer equal to or larger than 3 and equal to or smaller than 450. n represents an integer equal to or larger than 20 and equal to or smaller than 300.)

[7] The method of producing the porous metal oxide particles as described in any one of [3] to [6],
wherein the step of obtaining a mixture comprises a step of mixing the water and/or the organic solvent capable of dissolving a part or all of water, water dispersion of the water-insoluble polymer particles and the base catalyst.

[8] The method of producing the porous metal oxide particles as described in any one of [3] to [7],
wherein the aforementioned metal oxide precursor is mixed in a condition of being preliminarily diluted with an organic solvent miscible or partially miscible with water in the step of obtaining the organic and inorganic composite particles.

[9] A resin composition comprising the porous metal oxide particles as described in [11] or [2] and a binder resin.

[10] A film comprising the porous metal oxide particles as described in [1] or [2].

[11] A paint comprising the porous metal oxide particles as described in [1] or [2].

[12] A thermal insulation material comprising the porous metal oxide particles as described in [1] or [2].

[13] A low dielectric constant material comprising the porous metal oxide particles as described in [1] or [2].

[14] An ink comprising the porous metal oxide particles as described in [1] or [2].

[15] A medicinal agent adapting a drug delivery system (DDS) comprising the porous metal oxide particles as described in [1] or [2], wherein a drug is contained within the mesopores.

[16] A coating material containing a component (A) and a component (B):
(A) the metal oxide porous particles as described in [1] or [2]; and
(B) a curable functional group-containing compound.

[17] The coating material as described in [16],
wherein the component (B) is an activated energy beam-curable functional group-containing compound or a thermosetting functional group-containing silicon compound.

[18] The coating material as described in [16] or [17],
wherein ratio of the component (A) to 100 parts by weight of the components (A) and (B) in total is equal to or higher than 1 part by weight and equal to or lower than 60 parts by weight.

[19] A coating film obtained by curing the coating material as described in any one of [16] to [18].

[20] A film comprising the coating film as described in [19] in a surface section thereof.

[21] A lens comprising the coating film as described in [19] in a surface section thereof.

[22] An image display device comprising the coating film as described in [19] on the surface thereof.

Effect of the Invention

The porous metal oxide particle of the present invention can be used for various types of applications because of their smaller mean particle size and homogeneous particle sizes, and can effectively produce desired characteristics. For example, the porous metal oxide particles of the present invention can be easily uniformly dispersed to a binder resin to provide a resin composition having higher transparency.

Further, the metal oxide porous particles of the present invention have larger pore size of the mesopores as compared with that of the conventional particles, so that larger voids are contained in the inside of the particles. Thus, the particles have enhanced adsorption property, can include desired substances in the pores.

Also, the particles, which contain larger air layer within the particles, can contribute to improvements in the characteristics such as light weighting, thermal insulating properties, low refractive index, low dielectric constant and the like. Since the porous metal oxide particles of the present invention possess the above-described characteristics, these can be employed for various types of applications.

Also, the method of producing the porous metal oxide particles of the present invention has enhanced flexibility in the particle design, and proportion of mesopores (porosity) existing in one particle can be freely changed, so that the porous metal oxide particles of the present invention can be obtained with improved efficiency.

BRIEF DESCRIPTION OF THE DRAWINGS

The above and other objectives, advantages and features of the present invention will be more apparent from the following description of certain preferred embodiments taken in conjunction with the accompanying drawings.

DESCRIPTION OF EMBODIMENTS

Porous metal oxide particles of the present invention, methods of producing thereof, and applications thereof will be described on the basis of First embodiment and Second Embodiment as follows.

First Embodiment

Porous Metal oxide particles according to the present embodiment have 50% mean particle size by volume equal to or larger than 50 nm and equal to or smaller than 300 nm, a ratio of 90% mean particle size by volume to 50% mean particle size by volume (D90/D50) equal to or lower than 2.0, mesopores having pore size determined by Barrett-Joyner-Halenda method (BJH method) equal to or larger than 5 nm and equal to or smaller than 30 nm, and the pore having three-dimensional cubic phase structure.

The present embodiment will be described in reference to drawings when appropriate. In all drawings, an identical symbol is assigned to an identical composing element, and the detailed description thereof will be omitted when appropriate.

<Porous Metal Oxide Particles>

Figure 1:
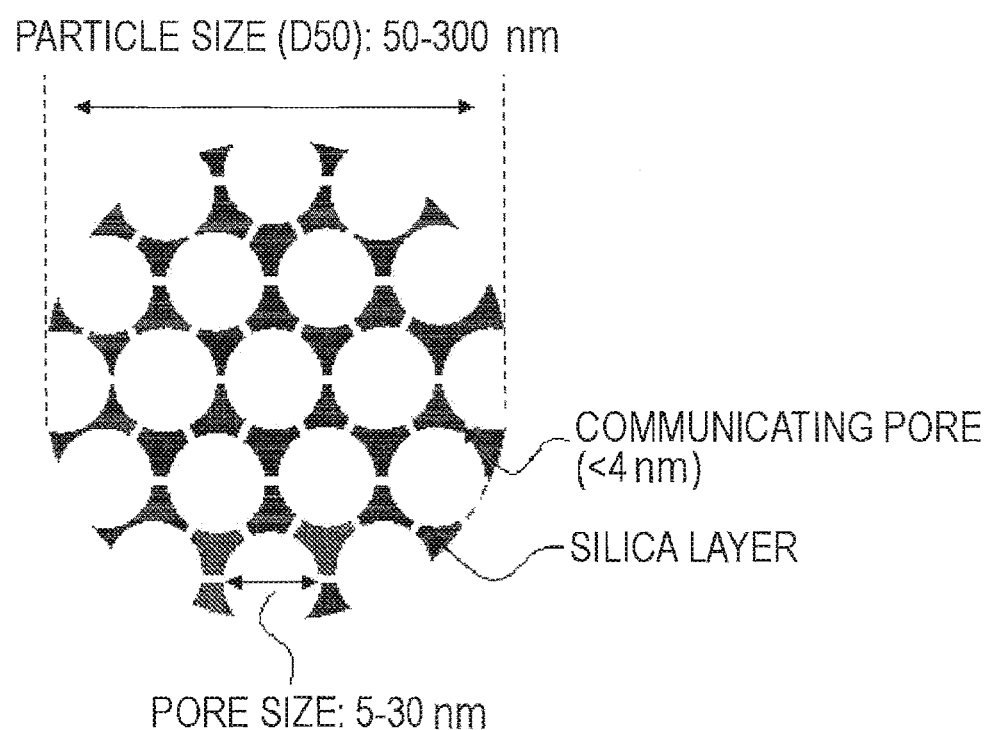
FIG. 1 is a schematic cross-sectional view, illustrating a porous metal oxide particle according to First Embodiment.

The porous metal oxide particles of the present embodiment are so-called monodisperse particles, substantially homogeneous in size and high in dispersibility. As shown in FIG. 1, the porous metal oxide particle has substantially homogeneous mesopores in the inside thereof, and the mesopores constitute a three-dimensional cubic phase structure, and these mesopores are connected to each other. The 50% mean particle size by volume of the porous metal oxide particles of the present embodiment is equal to or larger than 50 nm and equal to or smaller than 300 nm by the external size, and is preferably equal to or larger than 50 nm and equal to or smaller than 100 nm, and is more preferably equal to or larger than 60 nm and equal to or smaller than 90 nm. The particle sizes within this range allow easy production of the particles, and thus such particles can be used for various types of applications, in which desired characteristics can be effectively produced. For example, when these are used as a resin composition as will be discussed later, these can be uniformly dispersed in the binder resin to obtain a resin composition having enhanced transparency.

Also, in the porous metal oxide particles of the present embodiment, the ratio of 90% mean particle size by volume to 50% mean particle size by volume (D90/D50) is equal to or lower than 2.0, and is preferably equal to or lower than 1.5, and is more preferably equal to or higher than 1.0 and equal to or lower than 1.4. The ratios within this range can provide a narrower particle size distribution with reduced number of coarse particles, resulting in an enhanced handling ability and effective expression of desired characteristics. For example, when such particles are used as a resin composition as will be discussed later, such use is preferable in terms of uniform dispersibility in the binder resin and transparency of the obtained resin.

Also, the porous metal oxide particles of the present embodiment have mesopores, in which the BJH pore size is equal to or larger than 5 nm and equal to or smaller than 30 nm, and is preferably equal to or larger than 10 nm and equal to or smaller than 25 nm. The pore structure thereof is an ordered three-dimensional cubic phase structure. The porous metal oxide particles of the present embodiment are easily dispersed uniformly in a film or paint because of the monodispersibility of the particles, and exhibit enhanced transparency due to their smaller external size. Since the mesopores having the BJH pore size equal to or larger than 5 nm and equal to or smaller than 30 nm are contained, and the pore structure thereof is configured of an ordered three-dimensional cubic phase structure, large voids are contained within the particles. Therefore, a high adsorption property can be expected. Also, since large air layers are contained within the particles, characteristics such as light-weight, thermal insulating properties, low refractive index, low dielectric constant and the like can be expected.

The specific surface area of the porous metal oxide particles of the present embodiment is preferably equal to or larger than 80 m$^2$/g, and is more preferably equal to or larger than 100 m$^2$/g, and is particularly preferably equal to or larger than 150 m$^2$/g.

Also, in terms of thermal conductivity, it is more advantageous if there is no anisotropy derived from their shape, it is preferable to have a spherical shape and contain homogenous mesopores.

The external size of the porous metal oxide particle can be confirmed from a sample dispersed in water with a particle size distribution measurement apparatus according to dynamic light scattering (DLS). The size of the mesopore can be observed from image photographs of TEM, or alternatively can be calculated via the BJH method from adsorption isothermal curves of the nitrogen gas adsorption method. Alternatively, the sizes of the apertures connecting through the mesopores can be calculated via BJH method from desorption isothermal curves of the nitrogen gas adsorption method. In general, it can be evaluated that the structure is in a three-dimensional cubic phase structure if the peak of the desorption is different from that of the adsorption, and on the other hand, it can be evaluated that the structure is in a two-dimensional cylinder structure if these peaks are in substantially the same position.

In the present embodiment, examples of the metal include not only the typical metal materials but also include semi-metal such as silicon (Si). The metal oxide of the present embodiment is preferably an oxide of a metal selected from silicon (Si), aluminum (Al), zinc (Zn), zirconium (Zr), indium (In), tin (Sn), titanium (Ti), lead (Pb), hafnium (Hf), cobalt (Co), lithium (Li), barium (Ba), iron (Fe) and manganese (Mn), and in terms of the fact that the refractive index and the thermal conductivity of the material itself are relatively low among metal oxides, silicon oxide (silica) is particularly preferable.

Also, the metal oxide may be a composite oxide containing multiple metals.

<Method of Producing Porous Metal Oxide Particles>

The method of producing the porous metal oxide particles of the present embodiment comprises:

a step (1) of obtaining organic and inorganic composite particles by a sol-gel reaction of a metal oxide precursor in the presence of a water-insoluble polymer particles that is capable of being dispersed in a water-based medium; and a step (2) of removing the aforementioned water-insoluble polymer particles from the aforementioned organic and inorganic composite particles to obtain porous metal oxide particles.

The organic and inorganic composite particles obtained in the step (1) contains water-insoluble polymer particles in particles composed of metal oxide, and the water-insoluble polymer particles serving as the template are removed in the step (2) to produce the porous metal oxide particles of the present embodiment.

For more details, the step (1) comprises step (1-1) and step (1-2).

Step (1-1): a step of obtaining a mixture by adding water-insoluble polymer particles having 50% mean particle size by volume equal to or larger than 5 nm and equal to or smaller than 30 nm and a base catalyst in water and/or an organic solvent capable of dissolving a part of or all of water.

Step (1-2): a step of obtaining organic and inorganic composite particles by mixing a metal oxide precursor with the mixture obtained in the aforementioned step (1-1) and carrying out a sol-gel reaction of the metal oxide precursor.

As described above, it is necessary to conduct the sol-gel reaction of the metal oxide precursor with the base catalyst in the presence of the water-insoluble polymer particles in the present embodiment. The progress of the sol-gel reaction is accelerated by the base catalyst, and further, metal oxide precursor three-dimensionally forms a dense gel so as to contain the water-insoluble polymer particles therein to allow preferentially providing the organic and inorganic composite particles.

The respective steps will be sequentially described as follows.

[Step (1-1)]

Specifically, in step (1-1), water-insoluble polymer particles (X) (hereinafter referred to as "component" (X) when appropriate), water and/or an organic solvent capable of dissolving a part of or all of water (Y) (hereinafter referred to as "component" (Y) when appropriate) and a base catalyst (Z) (hereinafter referred to as "component" (Z) when appropriate) are mixed to prepared a mixture. It is preferable in step (1-1) to obtain a mixture by mixing a water dispersion of the water-insoluble polymer particles as will be discussed later, water and/or the organic solvent capable of dissolving a part of or all of water and the base catalyst.

The water-insoluble polymer particles (X) will be described in detail.

It is preferable that the water-insoluble polymer particles have 50% mean particle size by volume equal to or larger than 5 nm and equal to or smaller than 30 nm. The porous metal oxide particles obtained from the above-described water-insoluble polymer particles are used to achieve a transparent film or coating film with enhanced thermal insulation.

Concerning the method of measuring the external size, for example, a method using a particle size distribution analyzer (DLS), and a method of direct observation using a transmission electron microscope (TEM) or a scanning electron microscope (SEM), or the like are applicable.

Concerning the water-insoluble polymer particles (X) used in the present embodiment, polymer particles dispersible in water-based medium, such as polyolefin based, poly(meth)acrylic acid ester based, polystyrene based, polyurethane based, polyacrylonitrile based, polyvinyl chloride based, polyvinylidene chloride based, polyvinyl acetate based, or polybutadiene based polymer particles are preferable. In particular, polyolefin based water-insoluble polymer particles are prone to form the water-insoluble polymer particles having the external size equal to or smaller than 30 nm, and thus are preferably used. Terminal branched polyolefin based copolymer particles represented by the following general formula (1) are more preferable.

[Terminal Branched Polyolefin Based Copolymer Particle]

(1)

In the formula, A represents polyolefin chain. $R^1$ and $R^2$ represent hydrogen atom or alkyl group having 1 to 18 carbon atoms, and at least one of them is hydrogen atom, and $X^1$ and $X^2$, which may be the same or different groups, represent a group having straight or branched polyalkylene glycol group.

Number average molecular weight of the terminal branched polyolefin based copolymer particles represented by general formula (1) is equal to or lower than $2.5 \times 10^4$, and is preferably equal to or lower than $1.5 \times 10^4$, and is more preferably equal to or lower than $4.0 \times 10^3$. And on the other hand, it is preferably equal to or higher than $5.5 \times 10^2$, and is more preferably equal to or higher than $8 \times 10^2$. The above-described number average molecular weight is represented by the sum of number average molecular weight of polyolefin chain represented by A, number average molecular weight of groups having polyalkylene glycol groups represented by $X^1$ and $X^2$ and the additional molecular weights corresponding to $R^1$, $R^2$ and $C_2H$.

The number average molecular weight of the terminal branched polyolefin based copolymer particle within the above-described range provides tendency to enhance the stability of particles in the dispersion and to enhance the dispersibility into water and/or the organic solvent miscible or partially miscible with water, in the case of using the terminal branched polyolefin based copolymer particles as the dispersoid, and also allows easy preparation of the dispersion, and thus is preferable.

Polyolefin chain, which is A in general formula (1) is obtained by polymerizing olefin having 2 to 20 carbon atoms. Examples of olefins having 2 to 20 carbon atoms include alpha olefins such as ethylene, propylene, 1-butene, 1-hexene and the like. In this embodiment, this may be homopolymer or copolymer of these olefins, or alternatively may be copolymer with other polymeric unsaturated compound as far as the characteristics are not deteriorated. Among these olefins, ethylene, propylene and 1-butene are particularly preferable.

Number average molecular weight of polyolefin chain represented by A in general formula (1) measured by gel permeation chromatograph (GPC) is from 400 to 8,000, and is preferably from 500 to 4,000, and is more preferably from 500 to 2,000. Here, number average molecular weight is a value in terms of polystyrene.

Number average molecular weight of polyolefin chain represented by A within the above-described range provides a tendency to allow high crystallinity of the polyolefin moiety and enhanced stability of the dispersion, and also provides tendency to allow low melt viscosity and easy preparation of the dispersion, and thus is preferable.

Ratio of weight average molecular weight (Mw) to number average molecular weight (Mn) of polyolefin chain represented by A in general formula (1), or in other words, molecular weight distribution (Mw/Mn) that is measured by GPC, is not particularly limited, and is ordinarily from 1.0 to several tens, and is more preferably equal to or lower than 4.0, and more preferably equal to or lower than 3.0.

Molecular weight distribution (Mw/Mn) of polyolefin chain represented by A in general formula (1) within the above-described range is preferable, in views of such as shapes of the particles in the dispersion and uniformity of the particle size.

A weight average molecular weight (Mw), a number average molecular weight (Mn), and molecular weight distribution (Mw/Mn) of polyolefin chain represented by A determined by GPC can be measured, for example, using GPC-150, commercially available from Merck Millipore, under the following conditions.
Separation column: TSK GNH HT (column size: 7.5 mm in diameter; 300 mm in length);
Column temperature: 140 degrees C.;
Mobile phase: orthodichlorobenzene (commercially available from Wako Pure Chemical Industries, Ltd.);
Antioxidizing agent: butylhydroxytoluene (commercially available from Takeda Pharmaceutical Co., Ltd.) 0.025% by mass;
Moving rate: 1.0 ml/min.;
Sample concentration: 0.1% by mass;
Sample injection volume: 500 microliter; and
Detector: differential refractometer.

In addition to above, molecular weight of polyolefin chain represented by A can be determined by measuring molecular weight of polyolefin having unsaturated group in one terminal as will be discussed later, and subtracting molecular weight equivalency corresponding to such terminal therefrom.

$R^1$ and $R^2$ are hydrogen atom or hydrocarbon group having 1 to 18 carbon atoms, which are substituent groups bound to double bond in polyolefin constituting A, and are preferably hydrogen atom or alkyl group having 1 to 18 carbon atoms. Preferable alkyl groups are methyl group, ethyl group and propyl group.

In general formula (1), $X^1$ and $X^2$ are the same or different groups, and represent a functional group containing straight or branched polyalkylene glycol groups each having number average molecular weight of from 50 to 10,000. Examples of a branching form of branched polyalkylene glycol group include a branching via multivalent hydrocarbon groups or via nitrogen atoms or the like. Examples include a branching via a hydrocarbon group bound to two or more nitrogen atoms, oxygen atoms or sulfur atoms in addition to the main skeleton, or a branching via a nitrogen atom bound to two alkylene groups in addition to the main skeleton, or the like.

Number average molecular weight of the group having polyalkylene glycol group within the above-described range shows the tendency to enhance dispersibility of the particles, and also tends to exhibit low melt viscosity, which allows easy preparation of dispersion, and thus it is preferable.

$X^1$ and $X^2$ of general formula (1) having the above-described structure allows providing polymer particles composed of terminal branched polyolefin based copolymer having the particle size, in which 50% mean particle size by volume is equal to or larger than 5 nm and equal to or smaller than 30 nm, without a need for using a surfactant.

Preferable examples of $X^1$ and $X^2$ in general formula (1), each of which is same or different, are groups represented by general formula (2):

$$\text{-E-X}^3 \qquad (2)$$

(In the formula, E represents oxygen atom or sulfur atom, $X^3$ represents polyalkylene glycol group or group represented by general formula (3):

$$-R^3\text{-(G)}_m \qquad (3)$$

(In the formula, $R^3$ represents m+1 valent hydrocarbon group, G, which is the same or different groups, represents a group represented by $-OX^4$ or $-NX^5X^6$ ($X^4$ to $X^6$ represent a polyalkylene glycol group.), and m represents a number of bonds of $R^3$ with G and is an integer of from 1 to 10.))
or group represented by general formula (4):

$$\begin{array}{c} -N-X^7 \\ | \\ X^8 \end{array} \qquad (4)$$

(In the formula, $X^7$ and $X^8$, which are the same or different groups, represent a polyalkylene glycol group or group represented by the above-described general formula (3)).

Group represented by $R^3$ in general formula (3) is m+1 valent hydrocarbon group having 1 to 20 carbon atoms. m is an integer of 1 to 10, and is preferably an integer of 1 to 6, and is particularly preferably an integer of 1 to 2.

A preferable example of general formula (1) includes terminal branched polyolefin based copolymer, in which any one of $X^1$ and $X^2$ in general formula (1) is group represented by general formula (4). Further preferable example includes terminal branched polyolefin copolymer, in which one of $X^1$ and $X^2$ is group represented by general formula (4) and the other is group represented by general formula (2).

Other preferable example of general formula (1) includes terminal branched polyolefin based copolymer, in which any one of $X^1$ and $X^2$ in general formula (1) is group represented by general formula (2), and more preferably both of $X^1$ and $X^2$ are groups represented by general formula (2).

Further preferable structure of general formula (4) is group represented by general formula (5).

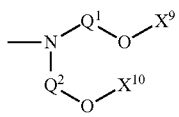
(5)

(In the formula, $X^9$ and $X^{10}$ are same or different and represent polyalkylene glycol groups, and $Q^1$ and $Q^2$ are same or different and respectively represent divalent hydrocarbon groups.)

Divalent hydrocarbon groups represented by $Q^1$ and $Q^2$ in general formula (5) are preferably divalent alkylene group, and are more preferably alkylene group having 1 to 20 carbon atoms. Alkylene group having 1 to 20 carbon atoms may or may not have substituent groups, which include, for example, ethylene group, methylethylene group, ethylethylene group, dimethylethylene group, phenylethylene group, chloromethylethylene group, bromomethylethylene group, methoxymethylethylene group, aryloxymethylethylene group, propylene group, trimethylene group, tetramethylene group, hexamethylene group, cyclohexylene group and the like. Preferable alkylene group is hydrocarbon based alkylene group, and is particularly preferably ethylene group and methylethylene group, and is more preferably ethylene group. $Q^1$ and $Q^2$ may be one type of alkylene group, or may include two or more types of alkylene groups co-existing therein.

Further preferable structure of $X^1$ and $X^2$ represented by general formula (1) is group represented by general formula (6).

(6)

(In the formula, $X^{11}$ represents polyalkylene glycol group.)

Polyalkylene glycol groups represented by $X^3$ to $X^{11}$ are groups obtained by conducting addition polymerization of alkylene oxides. Examples of Alkylene oxide constituting polyalkylene glycol group represented by $X^3$ to $X^1$ include ethylene oxide, propylene oxide, butylene oxide, styrene oxide, cyclohexene oxide, epichlorohydrin, epibromohydrin, methylglycidyl ether, allylglycidyl ether and the like. Among these, preferable choices are propylene oxide, ethylene oxide, butylene oxide and styrene oxide. More preferable choices are propylene oxide and ethylene oxide, and the most preferable choice is ethylene oxide. Polyalkylene glycol groups represented by $X^3$ to $X^{11}$ may be groups obtained by homopolymerization of these alkylene oxides, or may be groups obtained by copolymerization of two or more of these alkylene oxides. Examples of preferable polyalkylene glycol groups include polyethylene glycol group, polypropylene glycol group, or group obtained by copolymerization of polyethylene oxide and polypropylene oxide, and particularly preferable group is polyethylene glycol group.

$X^1$ and $X^2$ in general formula (1) having the above-described structure allows enhanced dispersibility in water and/or the organic solvent miscible or partially miscible with water in the case of using terminal branched polyolefin based copolymer particles of the present embodiment as the dispersoid, and thus is preferable.

It is preferable to use polymer represented by the following general formula (1a) or (1b) for the terminal branched polyolefin based copolymer particles that can be used in the present embodiment.

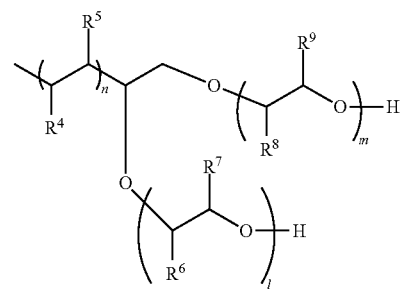
(1a)

(In the formula, $R^4$ and $R^5$ represent hydrogen atom or alkyl group having 1 to 18 carbon atoms and at least one of them is hydrogen atom. Alkyl group having 1 to 9 carbon atoms is preferable for alkyl group and alkyl group having 1 to 3 carbon atoms is further preferable. $R^6$ and $R^7$ represent hydrogen atom or methyl group and at least one thereof is hydrogen atom. $R^8$ and $R^9$ represent hydrogen atom or methyl group and at least one thereof is hydrogen atom.

$l+m$ represents an integer equal to or larger than 2 and equal to or smaller than 450, and is preferably an integer equal to or larger than 5 and equal to or smaller than 200.

n represents an integer equal to or larger than 20 and equal to or smaller than 300, and is preferably an integer equal to or larger than 25 and equal to or smaller than 200.)

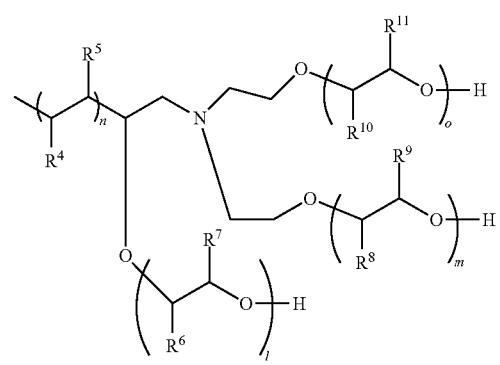
(1b)

(In the formula, $R^4$ and $R^5$ represent a hydrogen atom or an alkyl group having 1 to 18 carbon atoms and at least one of them is hydrogen atom. As the alkyl group, an alkyl group having 1 to 9 carbon atoms is preferable and an alkyl group having 1 to 3 carbon atoms is further preferable. $R^6$ and $R^7$ represent hydrogen atom or methyl group and at least one of them is a hydrogen atom. $R^8$ and $R^9$ represent hydrogen atom or methyl group and at least one thereof is hydrogen atom. $R^{10}$ and $R^{11}$ represent hydrogen atom or methyl group and at least one of them is hydrogen atom.

$l+m+o$ represents an integer equal to or larger than 3 and equal to or smaller than 450, and is preferably an integer equal to or larger than 5 and equal to or smaller than 200.

n represents an integer equal to or larger than 20 and equal to or smaller than 300, and is preferably an integer equal to or larger than 25 and equal to or smaller than 200.)

It is further preferable to use a polymer represented by the following general formula (1c) for the polymer represented by general formula (1b).

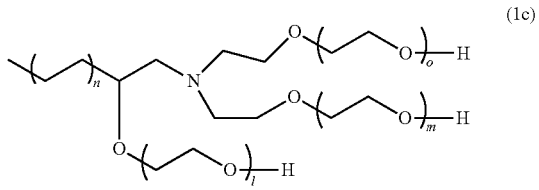

(1c)

(In the formula, l+m+o and n are identical to those in general formula (1b).)

Number of ethylene units in polyethylene chain (n) is calculated by dividing number average molecular weight (Mn) of polyolefin chain represented by A in general formula (1) by the molecular weight of ethylene unit. Also, total number of ethyleneglycol units in polyethylene glycol chain (l+m or l+m+o) can be calculated on the assumption that a weight ratio of raw material of polymer in the reaction of adding polyethylene glycol groups to ethylene oxide used is equivalent to the ratio of a number average molecular weight (Mn) of the raw material of polymer to that of polyethylene glycol group.

n, l+m or l+m+o can also be determined by $^1$H-NMR. For example, these can be calculated for a terminal branched polyolefin based copolymer (T) used in Example and dispersion particles containing thereof by using an integrated value of the methylene group (shift value: 1.06-1.50 ppm) in the polyolefin chain represented in A and an integrated value of the alkylene group (shift value: 3.33-3.72 ppm) in the polyethylene glycol (PEG), on the assumption that an integrated value of the terminal methyl group (shift value: 0.88 ppm) in polyolefin chain represented by A in general formula (1) is equivalent to 3 protons.

More specifically, since molecular weight of methyl group is 15, molecular weight of methylene group is 14, and molecular weight of ethylene oxide group is 44, number average molecular weight of polyolefin chain represented by A and alkylene group can be calculated from values of the respective integrated values. Number average molecular weight of polyolefin chain represented by A obtained here can be divided by molecular weight of ethylene unit to calculate n, and number average molecular weight of alkylene group is divided by molecular weight of ethyleneglycol unit to calculate total number (l+m or l+m+o) of ethyleneglycol units in PEG chain.

When polyolefin chain represented by A is composed of ethylene-propylene copolymer, both of the content of propylene that can be measured by IR, $^{13}$C-NMR or the like and the integrated value in $^1$H-NMR can be used to calculate n and l+m or l+m+o. A method of using internal standard in $^1$H-NMR is also effective.

The aforementioned terminal branched polyolefin based copolymer particles can be prepared by, for example, a method as described in WO2010/103856.

The polymer particles of the present embodiment composed of the above-described terminal branched polyolefin based copolymer are the rigid particles having a structure, in which polyolefin chain moiety represented by A in general formula (1) is oriented toward the inside and such polyolefin chain moiety has crystallinity.

The terminal branched polyolefin based copolymer particles of the present embodiment can also be dispersed in a liquid such as a solvent again even after the separation of the particles by drying the dispersion, since polyolefin chain moiety thereof has crystallinity. The terminal branched polyolefin based copolymer particle of the present embodiment is a rigid particle, in which melting point of polyolefin chain moiety included in the particle is preferably equal to or higher than 80 degrees C., and is more preferably equal to or higher than 90 degrees C.

The melting point of polyolefin chain moiety of equal to or higher than the above-described temperature allows providing rigid particle having better crystallinity, such that collapse of particle is restrained even though the particle is heated to higher temperature.

Thus, since the collapse of the particle is restrained in the manufacturing process or in the situation of use on various types of applications as will be discussed later, the yield of the product and the quality of the product are further stabilized without deteriorating the characteristics of the terminal branched polyolefin based copolymer particles of the present embodiment.

The terminal branched polyolefin based copolymer particles of the present embodiment exhibit a constant particle size regardless of dilution concentration even if it is dispersed to a solvent. In other words, these particles are redispersible and constant in size, and therefore these particles are different from micelle particles dispersing in a liquid.

[Non-Water-Soluble Polymer Particle Dispersion]

The dispersion of the present embodiment contains the above-described water-insoluble polymer particles, preferably the aforementioned terminal branched polyolefin based copolymer particles, as a dispersoid, and such dispersoid is dispersed as particles in water and/or the organic solvent capable of dissolving a part of or all of water.

In the present embodiment, the dispersion formed by dispersing the water-insoluble polymer particles includes any one of, for example:

(1) a dispersion obtained during the production of the water-insoluble polymer particles, which contains the polymer particles;

(2) a dispersion obtained by additionally dispersing or dissolving other dispersoids or additives in the dispersion containing the water-insoluble polymer particles obtained in the production of the polymer particles; and (3) a dispersion obtained by dispersing the water-insoluble polymer particles in water or an organic solvent having an affinity for water with additionally dispersing or dissolving other dispersoids or additives.

Ratio of the aforementioned water-insoluble polymer particles contained in the dispersion of the present embodiment is preferably from 0.1 to 50% by mass provided that whole dispersion is 100% by mass, and is more preferably from 1 to 40% by mass, and is further preferably from 1 to 20% by mass.

The ratio of the contained water-insoluble polymer particles within the above-described range allows providing enhanced practicality of the dispersion and maintaining appropriate level of viscosity, and providing easy handling, and thus is preferable.

In addition, the 50% mean particle size by volume of the particles in the dispersion of the present embodiment is preferably equal to or larger than 5 nm and equal to or smaller than 30 nm.

The 50% mean particle size by volume of particle can be suitably controlled by changing the molecular weight, ratio of hydrophilic group to lipophilic group, the degree of branch of the water-insoluble polymer and the like.

For example, this can be adjusted by suitably changing the structure of polyolefin moiety in the aforementioned terminal branched polyolefin based copolymer and the structure of terminal branch moiety.

Here, the 50% mean particle size by volume in the present embodiment means the diameter of the particle at the time that the cumulative volume reaches to 50% provided that the whole volume is 100%, and can be measured by using a dynamic light scattering particle size distribution analyzer or a microtruck particle size analyzer.

In addition, the shape thereof can be observed by a transmission electron microscope (TEM) after it is negatively stained with, for example, phosphotungstic acid.

The dispersion in the present embodiment is obtained by dispersing the water-insoluble polymer particles in water and/or an organic solvent miscible or partially miscible with water.

The dispersing in the present embodiment can be achieved via a method of physically dispersing the water-insoluble polymer particles in water and/or the organic solvent miscible or partially miscible with water with mechanical shear force.

The dispersing method is not particularly limited to any specific method, and various types of dispersing methods can be used. More specifically, examples of available methods include: a method of dispersing a molten mixture with a high pressure homogenizer, a high pressure homomixer, an extruding kneader, an autoclave or the like, in which the molten mixture is made by mixing the water-insoluble polymer particles with water and/or the organic solvent capable of dissolving a part of or all of water and then making the mixture into the molten state; a method of injection-pulverizing at a high pressure; and a method of atomizing through a spray nozzle. In addition, available method may alternatively be a method of preliminarily dissolving the aforementioned water-insoluble polymer particles in a solvent other than water, and then mixing the resultant mixture with water and/or the organic solvent miscible or partially miscible with water, and then dispersing the mixture with a high pressure homogenizer, a high pressure homomixer or the like. In such case, the solvent used for the dissolution of the water-insoluble polymer particles is not particularly limited as long as the water-insoluble polymer particles can be dissolved, and examples include toluene, cyclohexane, or organic solvents exhibiting better affinity with water. If an incorporation of an organic solvent other than water in the dispersion is not preferable, such incorporated solvent can be removed by an operation such as a distillation or the like.

Furthermore specifically, the dispersion can be obtained by thermally stirring while applying shear force in, for example, an auto clave with stirrer that can apply shear force, at a temperature, at which the water-insoluble polymer particles are in molten state and are not deteriorated by the heating, specifically for example, equal to or higher than 100 degrees C. and preferably from 120 to 200 degrees C. in the case of that the aforementioned water-insoluble polymer particles are the terminal branched polyolefin based copolymer particles.

Time required for dispersing is, depending upon the dispersing temperature and other dispersing conditions, on the order of from 1 to 300 minutes. The dispersing can be sufficiently conducted and the water-insoluble polymer particles are hard to be deteriorated within the above-described stirring time, and thus such time duration is preferable. It is preferable after the reaction to maintain the shear force-applying state until the temperature in the dispersion is equal to or lower than 100 degrees C., preferably equal to or lower than 60 degrees C.

While an addition of a surfactant is not indispensable in the production of the dispersion used in the present embodiment, for example, an anionic surfactant, a cationic surfactant, an ampholytic surfactant, a nonionic surfactant or the like may be present therewith.

Examples of anionic surfactant include: carboxylate, simple alkyl sulfonate, modified alkyl sulfonate, alkyl allyl sulfonate, alkylsulfuric acid ester salt, sulfate oil, sulfate ester, fatty acid monoglyceride sulfate, alkanolamide sulfate, ether sulfate, alkyl phosphate, alkyl benzene phosphonate, naphthalenesulfonate formaldehyde condensate and the like.

Examples of cationic surfactant includes: simple amine salt, modified amine salt, tetraalkyl quaternary ammonium salt, modified trialkyl quaternary ammonium salt, trialkyl benzyl quaternary ammonium salt, modified trialkyl benzyl quaternary ammonium salt, alkyl pyridinium salt, modified alkyl pyridinium salt, alkyl quinolinium salt, alkyl phosphonium salt, alkyl sulfonium salt and the like.

Examples of ampholytic surfactant include, for example: betaine, sulfobetaine, sulfate betaine and the like.

Examples of nonionic surfactant include, for example: fatty acid monoglycerin ester, fatty acid polyglycol ester, fatty acid sorbitan ester, fatty acid sucrose ester, fatty acid alkanol amide, fatty acid polyethylene glycol condensate, fatty amide polyethylene glycol condensate, fatty acid alcohol polyethylene glycol condensate, fatty acid amine polyethylene glycol condensate, fatty acid mercaptan polyethylene glycol condensate, alkyl phenol polyethylene glycol condensate, polypropylene glycol polyethylene glycol condensate and the like. One of these surfactants may be used alone, or two or more of these surfactants may also be used.

In the process of producing the dispersion used in the present embodiment, a filtration step may be added to the process for the purpose of eliminating contaminants. In such case, for example, a stainless-steel filter (wire diameter 0.035 mm, plain weave) of about 300 mesh may be installed to carry out a pressure filtration (air pressure 0.2 MPa).

In the dispersion obtained by the above-described method, none of agglomeration and precipitation is caused even if pH is changed from 1 to 13 by adding various types of acid and base, for example, an acid such as hydrochloric acid, sulfuric acid, phosphoric acid and the like, and/or a base such as potassium hydroxide, sodium hydroxide, calcium hydroxide and the like. In addition, none of agglomeration and precipitation is caused even if this dispersion is placed under ordinary pressure at a temperature within broader range, which causes repetitions of heating and reflux or freezing and thawing.

Water in the above-described method is not particularly limited, and distilled water, ion-exchange water, urban water, industrial water or the like may be used, however, distilled water and ion-exchange water are preferably used.

In addition, the organic solvent exhibiting better affinity with water in the above-described method is not particularly limited as long as the dispersoid such as water-insoluble polymer particles or surfactant can be dispersed therein, and examples include, ethyleneglycol, tetraethylene glycol, isopropyl alcohol, acetone, acetonitrile, methanol, ethanol, dimethylsulfoxide, dimethylformamide, dimethyl imidazolidinone and the like. If an incorporation of an organic solvent in the dispersion is not preferable, such organic solvent can be removed by an operation such as a distillation or the like after the dispersion containing the dispersoid is prepared.

The dispersion in the present embodiment preferably contains from 0.001 parts by mass to 20 parts by mass, more preferably from 0.01 parts by mass to 10 parts by mass, further preferably from 0.1 parts by mass to 5 parts by mass, of a dispersoid except the terminal branched polyolefin based copolymer particles, provided that the aforementioned water-insoluble polymer particles are 100 parts by mass. The content of the dispersoid within the above-described range provides practically enhanced physical properties and difficulty in causing agglomeration and precipitation, and thus is preferable.

[Water and/or Organic Solvent Miscible or Partially Miscible with Water (Y)]

The component (Y) in the present embodiment is added for the purpose of further hydrolyzing a metal oxide precursor (W) (hereinafter, appropriately referred to as "component" (W)).

In addition, examples of the component (Y) include a solvent to use for obtaining an aqueous dispersion by using the water-insoluble polymer, a solvent to use for mixing the aqueous dispersion, metal alkoxide, and/or partial hydrolysis condensate, a component (Z) of a catalyst for sol-gel reaction which will be described later, and a solvent to use for mixing the metal oxide precursor (W) which will be described later.

Water is not particularly limited, and distilled water, ion-exchange water, urban water, industrial water or the like may be used, and distilled water and ion-exchange water are preferably used.

The organic solvent miscible or partially miscible with water is not particularly limited as long as the organic solvent exhibits a better affinity for water and is capable of dispersing the water-insoluble polymer, and examples includes, methanol, ethanol, propyl alcohol, isopropyl alcohol, acetone, acetonitrile, dimethylsulfoxide, dimethylformamide, dimethyl imidazolidinone, ethyleneglycol, tetraethylene glycol, dimethylacetamide, N-methyl-2-pyrrolidone, tetrahydrofuran, dioxane, methyl ethyl ketone, cyclohexanone, cyclopentanone, 2-methoxyethanol (methyl cellosolve), 2-ethoxyethanol (ethyl cellosolve), ethyl acetate and the like. Among these, methanol, ethanol, propyl alcohol, isopropyl alcohol, acetonitrile, dimethylsulfoxide, dimethylformamide, acetone, tetrahydrofuran and dioxane are preferable, since these exhibit enhanced affinity with water. When these organic solvents are contained in the mixture, the particle size and shape can be suitably controlled in the condensation of the metal oxide precursor, such that the obtained product can be approached to spherical fine particles with homogeneous sizes. Furthermore, since tetraethoxysilane (TEOS) and tetramethoxysilane (TMOS) are preferable for the component (W) as will be discussed later, alcohols such as ethanol and methanol are particularly preferable.

[Base Catalyst (Z)]

In the mixture composition used in the present embodiment, a base catalyst is preferably used, in terms of suitably controlling the condensation rate of the metal oxide precursor and creating spherical porous metal oxide materials. More specifically, this includes: ammonia; ammonium hydroxide (aqueous ammonia); alkali metal hydroxide such as potassium hydroxide, sodium hydroxide and the like; quaternary ammonium hydroxide such as tetramethylammonium hydroxide, tetraethylammonium hydroxide, tetrabutylammonium hydroxide and the like; amines such as triethylamine, tributylamine, morpholine, pyridine, piperidine, ethylenediamine, diethylenetriamine, ethanolamine, diethanolamine, triethanolamine and the like; amino silanes such as 3-aminopropyltriethoxysilane, N-(2-aminoethyl)-3-aminopropyltrimethoxysilane and the like. Most preferably, ammonia and ammonium hydroxide (aqueous ammonia) are used, in terms of easily controlling the particle size and shape of the porous metal oxide material, and ammonium hydroxide (aqueous ammonia) is further preferable in terms of the safety.

[Step (1-2)]

In the step (1-2), the metal oxide precursor (W) is mixed to the mixture obtained in the aforementioned step (1-1), and the sol-gel reaction is conducted to obtain the organic and inorganic composite particles.

[Metal Oxide Precursor (W)]

Examples of metal oxide precursor include a metalalkoxide and/or a partial hydrolysis condensate thereof, a metal halide, a metal acetate, a metal nitrate, a metal sulfate and the like.

The metal alkoxides in the present embodiment mean compounds represented by the following formula (12).

$$(R^{12})_{x_1}M(OR^{13})_{y_1} \qquad (12)$$

In this formula, $R^{12}$ represents hydrogen atom, alkyl group (methyl group, ethyl group, propyl group or the like), aryl group (phenyl group, tolyl group or the like), carbon-carbon double bond-containing organic group (acryloyl group, methacryloyl group, vinyl group or the like), halogen-containing group (halogenated alkyl groups such as chloropropyl group, fluoromethyl group or the like) and the like. $R^{13}$ represents lower alkyl group having 1 to 6 carbon atoms, preferably having 1 to 4 carbon atoms. $x_1$ and $y_1$ represent an integer so that $x_1+y_1=4$ and $x_1$ is equal to or smaller than 2. Examples of M include Li, Na, Mg, Al, Si, K, Ca, Sc, Ti, V, Cr, Mn, Fe, Co, Ni, Cu, Zn, Rb, Sr, Y, Nb, Zr, Mo, Ag, Cd, In, Sn, Sb, Cs, Ba, La, Ta, Hf, W, Ir, Tl, Pb, Bi, rare earth metals and the like, and metals (alkoxide), which are capable of creating colorless metal oxide by a sol-gel reaction, such as Si, Al, Zn, Zr, In, Sn, Ti, Pb, Hf and the like are preferable, in terms of the availability to use as an optical material. Among these, silicon (Si), aluminum (Al), zirconium (Zr), titanium (Ti) and the like are preferably used, and these may be used in combination. Among these, silicon compounds have higher Industrial availability since these are relatively cheap and easily obtainable, and reactions therewith moderately progress. In addition, the metal alkoxide and/or the hydrolytic condensate thereof may be a compound, which is capable of creating a metal oxide as will be discussed later via a sol-gel reaction by addition of a catalyst and water.

Specific examples thereof include: alkoxy silanes such as tetramethoxysilane (TMOS), tetraethoxysilane (TEOS), tetrapropoxysilane, tetraisopropoxy silane, methyl trimethoxysilane, methyl triethoxysilane, methyl tripropoxysilane, methyl tributoxysilane, ethyl trimethoxysilane, ethyl triethoxysilane, n-propyl trimethoxysilane, n-propyl triethoxysilane, isopropyl trimethoxysilane, isopropyl triethoxysilane, dimethyl dimethoxysilane, dimethyl diethoxysilane, diphenyl dimethoxysilane, diphenyl diethoxysilane, vinyl trimethoxysilane, vinyl triethoxysilane, phenyl trimethoxysilane, phenyl triethoxysilane, p-styryl trimethoxysilane, 3-methacryloxypropyl methyl dimethoxysilane, 3-methacryloxypropyl methyl diethoxysilane, 3-methacryloxypropyl trimethoxysilane, 3-methacryloxypropyl triethoxysilane, 3-acryloxypropyl trimethoxysilane, 3-acryloxypropyl triethoxysilane, 3-chloropropyl triethoxysilane, trifluoromethyl trimethoxysilane, trifluoromethyl triethoxysilane and the like; alkoxy aluminum; alkoxy zirconium; alkoxy titanium and the like associated therewith.

Further, in addition to these metal alkoxides, metal alkoxides having various types of functional groups in $R^{12}$ described in the following 1) to 4) may also be used.

1) compounds having amino group and alkoxysilyl group such as 3-aminopropyl trimethoxysilane, 3-aminopropyl triethoxysilane, 3-aminopropyl methyl dimethoxysilane, 3-aminopropyl methyl diethoxysilane, N-2-(aminoethyl)-3-aminopropyl methyl dimethoxysilane, N-2-(aminoethyl)-3-aminopropyl trimethoxysilane, 2-aminoethylamino methyl trimethoxysilane, 3-aminopropyl dimethyl ethoxysilane, 2-(2-aminoethyl thioethyl)triethoxysilane, p-aminophenyl trimethoxysilane, N-phenyl-3-aminopropyl methyl dimethoxysilane, N-phenyl-3-aminopropyl methyl diethoxysilane, N-phenyl-3-aminopropyl trimethoxysilane, N-phenyl-3-aminopropyl triethoxysilane and the like.
2) compounds having glycidyl group and alkoxysilyl group such as 3-glycidoxypropyl propyl trimethoxysilane, 3-glycidoxypropyl propyl triethoxysilane, 3-glycidoxypropyl methyl diethoxysilane and the like.
3) compounds having thiol group and alkoxysilyl group such as 3-mercaptopropyl methyl dimethoxysilane, 3-mercaptopropyl trimethoxysilane and the like.
4) compounds having ureido group and alkoxysilyl group such as 3-ureidopropyl trimethoxysilane and the like.

In the present embodiment, preferable metal alkoxides include alkoxysilane, in which M in the above-described formula (12) is silicon (Si); alkoxy zirconium, in which M is zirconium (Zr); alkoxy aluminum, in which M is aluminum (Al); and alkoxy titanium, in which is titanium (Ti).

The partial hydrolysis condensate of metal alkoxide is a compound obtained by polycondensation of a partially hydrolyzed product of one or more of these metal alkoxides that is partially hydrolyzed by using base catalyst (Z), and is typically, for example, a partial hydrolysis polycondensation compound of a metal alkoxide.

In the present embodiment, preferable partial hydrolysis condensates of metal alkoxides include condensates of alkoxysilanes, condensates of alkoxy zirconiums, condensates of alkoxy aluminums and condensates of alkoxy titaniums.

Examples of the metal halides available in the present embodiment include compounds represented by the following formula (13).

$(R^{14})x_2 MZ y_2$      (13)

In the formula, $R^{14}$ represents hydrogen atom, alkyl group (methyl group, ethyl group, propyl group and the like), alkoxy group (methoxy group, ethoxy group, propoxy group, butoxy group and the like), aryl group (phenyl group, tolyl group and the like), carbon-carbon double bond-containing organic group (acryloyl group, methacryloyl group, vinyl group and the like) or halogen-containing group (halogenated alkyl groups such as chloropropyl group, fluoromethyl group and the like). Z represents F, Cl, Br or I. $x_2$ and $y_2$ represent an integer so that $x_2+y_2 \leq 4$ and $x_2$ is equal to or smaller than 2. Examples of M include Li, Na, Mg, Al, Si, K, Ca, Sc, Ti, V, Cr, Mn, Fe, Co, Ni, Cu, Zn, Rb, Sr, Y, Nb, Zr, Mo, Ag, Cd, In, Sn, Sb, Cs, Ba, La, Ta, Hf, W, Ir, Tl, Pb, Bi, rare earth metals and the like, and metals (alkoxide), which are capable of creating colorless metal oxide by a sol-gel reaction, such as Si, Al, Zn, Zr, In, Sn, Ti, Pb, Hf and the like are preferable, in terms of the availability to use as an optical material. Among these, silicon (Si), aluminum (Al), zirconium (Zr), titanium (Ti) and the like are preferably used, and these may be used in combination.

Specific examples thereof include tetrachloro-dimethyl disilane, chloropropyl dichloromethylsilane, chloromethyl (dichloro)methylsilane, di-tert-butyl dichlorosilane, dibutyl-dichlorosilane, dichloro(methyl)-n-octylsilane, dichloro(m-ethyl)phenylsilane, dichlorocyclohexylmethylsilane, dichlorodiethylsilane, dichlorodihexylsilane, dichlorodiisopropylsilane, dichlorodimethylsilane, dichlorodiphenylsilane, dichloroethylsilane, dichlorohexylmethylsilane, dichloromethylsilane, dichloromethylvinylsilane, tetrachlorosilane, 1,2-bis(trichlorosilyl)ethane, 3-chloropropyl trichlorosilane, allyltrichlorosilane, butyltrichlorosilane, cyclohexyltrichlorosilane, ethyltrichlorosilane, hexachlorodisilane, hexachlorodisilane, phenyltrichlorosilane, thexyltrichlorosilane, trichloro(methyl)silane, trichloro(propyl)silane, trichlorohexylsilane, trichlorosilane, and trichlorovinylsilane; and the corresponding fluorosilanes, bromosilanes and iodosilanes; and, the corresponding aluminum halide, zirconium halide, titanium halide, cobalt halide, lithium halide, barium halide, iron halide, and manganese halide; and hydrates thereof.

In the present embodiment, examples of metal acetate typically include cobalt acetate, cobalt acetoacetate, lithium acetate, lithium acetoacetate, iron acetate, iron acetoacetate, manganese acetate, manganese acetoacetate, or hydrates thereof. Examples of metal nitrate include cobalt nitrate, lithium nitrate, iron nitrate, manganese nitrate, or hydrates thereof. Examples of metal sulfates include titanium sulfate, zirconium sulfate, indium sulfate, zinc sulfate, selenium sulfate, antimony sulfate, tin sulfate, yttrium sulfate or hydrates thereof.

The metal alkoxide and/or the partial hydrolysis condensate are preferable as the component (W) in the applications of the present embodiment, and alkoxysilane is more preferable as the metal alkoxide, and in particular, tetraethoxysilane (TEOS) and tetramethoxysilane (TMOS) are particularly preferable, due to their better handling-ability.

[Mixing Ratio of Component (X) to Component (W)]

The mixing ratio of the water-insoluble polymer particles (X) to the metal oxide precursor (W) is not particularly limited, and is preferably from 1:10 to 10:1. When the amount of the components (X) is large, the proportion of the metal oxide becomes low, resulting in poor control on the porous structure, and walls between the pores become thin, leading to deteriorated mechanical strength. When the amount of the components (W) is large, the proportion of the pores becomes low, resulting in small surface area and porosity, which offers little hope for performances as the porous material. The amount of water and/or the organic solvent capable of dissolving a part of or all of water (Y) to 100 parts of the metal oxide precursor (W) by weight is preferably equal to or larger than 30 parts by weight and equal to or smaller than 100000 parts by weight, and is more preferably equal to or larger than 50 parts by weight and equal to or smaller than 50000 parts by weight. A lower ratio of the component (Y) results in easier agglomeration of the particles, and a higher ratio is not preferable in terms of the production efficiency. Moreover, even though a ratio of water to the solvent in the component (Y) is not particularly limited, it is preferably in a range from 0.1:100 to 1:50. A lower ratio of water results in considerably reduced rate of the sol-gel reaction of the metal oxide precursor condensate, and a higher ratio causes a higher reaction rate, leading to the difficulty in the control of the particle size and shape. The amount of a catalyst (Z) for the sol-gel reaction to 100 parts of the metal oxide precursor (W) by weight is preferably equal to or larger than 10 parts by weight and equal to or smaller than 1000 parts by weight. A lower ratio of the component (Z) results in considerably reduced rate of the sol-gel reaction of the metal oxide precursor condensate, and a higher ratio causes larger particle sizes, resulting in the difficulty in obtaining the particles of equal to or smaller than 300 nm.

In the aforementioned step (1-2), it is preferable for a method of mixing the component (W) in the mixture obtained in the aforementioned step (1-1) to carry out the mixing of the component (W) in the state that such component is preliminarily diluted in the organic solvent miscible or partially miscible with water. Preliminary dilution with the organic solvent allows inhibiting a local reaction in the solution containing the existing catalyst (Z) for the sol-gel reaction, so that the particle size and shape of the porous metal oxide material are easily controlled. When diluted with the organic solvent, the amount to 100 parts of component (W) by weight is, for example, equal to or larger than 10 parts by weight and equal to or smaller than 10000 parts by weight, and is more preferably equal to or larger than 100 parts by weight and equal to or smaller than 1000 parts by weight. A lower dilution ratio results in a lesser degree of the effects, and a higher ratio is not preferable in terms of the production efficiency. Methanol, ethanol, propyl alcohol and isopropyl alcohol are preferable as the organic solvent miscible or partially miscible with water. When tetraethoxysilane (TEOS) or tetramethoxysilane (TMOS) is used as the metal alkoxide, ethanol and methanol are particularly preferable.

Also, preferable reaction temperature of the sol-gel reaction of the component (W) is equal to or higher than 1 degree C. and equal to or lower than 200 degrees C., and is more preferably equal to or higher than 10 degrees C. and equal to or lower than 100 degrees C., and is equal to or higher than 20 degrees C. and equal to or lower than 50 degrees C. A lower temperature results in a reduced reaction rate, which tends to cause uneven particle sizes and shape. A higher temperature causes volatilization of the ammonia serving as a catalyst, and hence makes control of the particle size difficult. The reaction time is equal to or longer than 10 minutes and equal to or shorter than 72 hours, in terms of the production yield and the production efficiency, and is more preferably equal to or longer than 1 hour and equal to or shorter than 24 hours. Even though the component (W) undergoes a sol-gel reaction under atmospheric pressure, the reaction alternatively can be carried out under higher pressure using an autoclave and the like.

Figure 2:
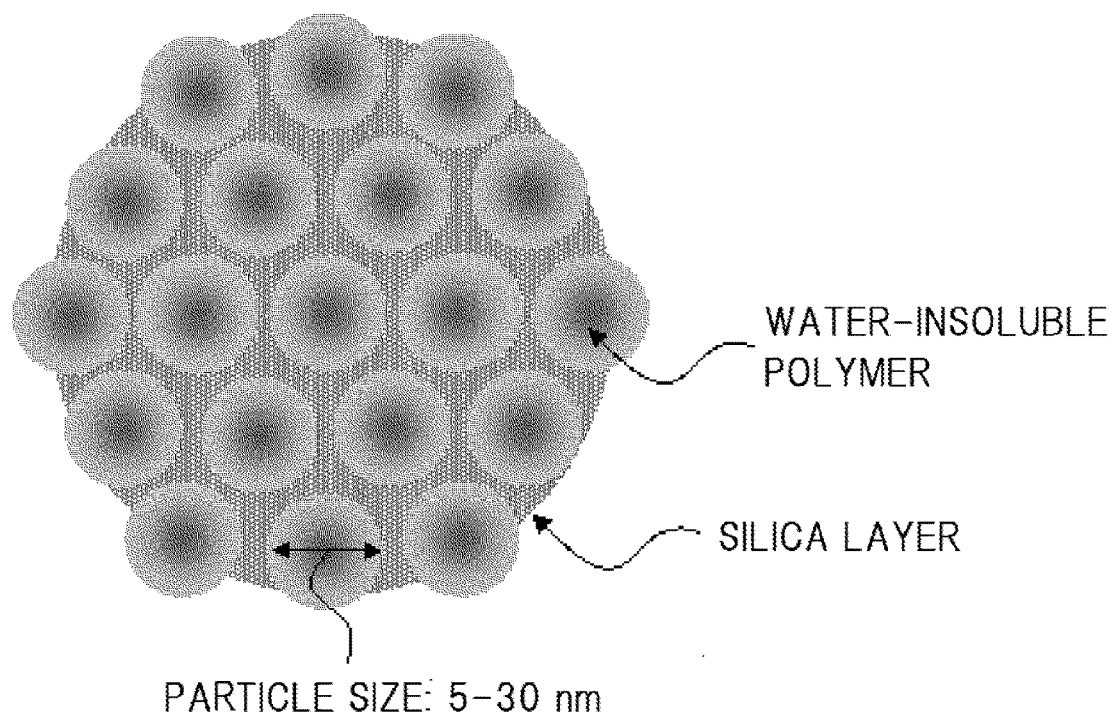
FIG. 2 is a schematic cross-sectional view, illustrating the organic and inorganic composite particle in First Embodiment.

As the metal oxide precursor condensate undergoes a sol-gel reaction, the organic and inorganic composite particles are formed. FIG. 2 is a schematic cross-sectional view, illustrating organic and inorganic composite particles according to the present embodiment.

The obtained organic and inorganic composite particles are recovered from the reaction solution by a method such as centrifugal separation or the like. The recovered organic and inorganic composite particles are washed with an organic solvent to remove the catalyst for the sol-gel reaction and water in order to finalize the sol-gel reaction, and then are sufficiently dried. Here, the state that the sol-gel reaction is finalized means ideally a condition, in which all creates M-O-M bonds, but in reality, contains a condition, which transitions to the state of solid (gel), although some alkoxyl group (M-OR$^2$) and M-OH group remains.

[Step (2)]

In step (2), the water-insoluble polymer particles are removed from the organic and inorganic composite particles to prepare the porous metal oxide particles.

Examples of the methods of removing the water-insoluble polymer particles includes a method of decomposing them off by calcination, a method of decomposing them off by applying VUV ray (vacuum ultraviolet radiation), far infra-red ray, microwave or plasma, a method of extracting them off by using a solvent and water and the like. In the case of decomposing the particles off by calcination, preferable temperature is from 200 degrees C. to 1000 degrees C., and is more preferably from 300 degrees C. to 700 degrees C. Excessively low calcination temperature causes failure in removing the water-insoluble polymer particles, and on the other hand excessively high calcination temperature may cause collapse of the pore as the temperature is closer to the melting point of metal oxide. The calcination may be carried out at a constant temperature, or a gradual temperature elevation from the room temperature may also be employed. Time for the calcination process is variable depending upon the temperature, and the process may be preferably conducted for the duration within the range of from 1 hour to 24 hours. The calcination may be carried out within an air atmosphere, or may be carried out within an atmosphere of an inert gas such as nitrogen, argon and the like. Alternatively, this may be carried out under reduced pressure, or in vacuum. In the case of decomposing the particles off by applying VUV ray, a VUV lamp, an excimer laser, or an excimer lamp may be used. An oxidative effect of ozone ($O_3$) generated during the radiation of VUV ray may be jointly utilized. The frequency of the microwave may be 2.45 GHz or 28 GHz. The output level of the microwave is not particularly limited, and the condition for successfully removing the water-insoluble polymer particles is selected.

When the extraction is conducted by using the solvent or water, the examples of the solvent include, ethyleneglycol, tetraethylene glycol, isopropyl alcohol, acetone, acetonitrile, methanol, ethanol, cyclohexane, dimethylsulfoxide, dimethylformamide, dimethylimidazolidinone, xylene, toluene, chloroform, dichloromethane and the like. The operation of the extraction may be conducted while heating. Alternatively, an ultrasonic (US) processing may be jointly used. In addition to above, after the extracting operation, it is preferable to conduct a thermal processing under a reduced pressure in order to remove water and the solvent remaining in the pores.

An anionic surfactant, a cationic surfactant, an ampholytic surfactant and a nonionic surfactant or the like, as described in the aforementioned method of dispersing the terminal branched polyolefin based copolymer particles, may coexist with the porous metal oxide particles, in order to improve the dispersing stability to water.

The porous metal oxide particles may be surface-treated with an organosilicic compound (surface treatment agent) typified by a silane coupling agent, in order to improve the dispersing stability to water, or in order to enhance the compatibility with the binder resin to improve the mechanical strength or the water resistance.

The method of the surface treatment may be conducted by a known method, and silane coupling agents preferably used are methyl trimethoxysilane, methyl triethoxysilane, methyl trichlorosilane, dimethyldichlorosilane, trimethylchlorosilane, vinyl trimethoxysilane, vinyl triethoxysilane, vinyl trichlorosilane, vinyl triacetoxysilane, vinyl tris(2-methoxyethoxy)silane, 3-methacryloyloxypropyl trimethoxysilane, 3-methacryloyloxypropyl tris(2-methoxyethoxy)silane, 3-chloropropyl trimethoxysilane, 3-chloropropyl methyl dimethoxysilane, 3-glycidyloxypropyl trimethoxysilane, 3-glycidyloxypropyl methyl diethoxysilane, 2-(3,4-epoxycyclohexyl)ethyl trimethoxysilane, 5,6-epoxyhexyl triethoxysilane, 3-ethyl-3-[3-(triethoxysilyl)propoxymethyl]oxetane, N-phenyl-γ-aminopropyltrimethoxysilane, hexamethyldisilazane and the like. In particular, when the monomer is polymerized via a cationic polymerization, the preferable choice includes silane coupling agents having functional groups polymerizable via a cationic polymerization, that are 3-glycidyloxypropyl trimethoxysilane, 3-glycidyloxypropyl methyl diethoxysilane, 2-(3,4-epoxycyclohexyl)ethyl trimethoxysilane, 5,6-epoxyhexyl triethoxysilane, 3-ethyl-3-[3-(triethoxysilyl)propoxymethyl] oxetane and the like. The above-described silane coupling agent may be used alone, or a combination of two or more thereof may be used.

[Method of Evaluating Porous Metal Oxide Particles]

The confirmation of the structure and the confirmation of the pore size of the porous metal oxide particles obtained in the present embodiment may be conducted with a transmission electron microscope (TEM/Transmission electron microscope JEM-2010F commercially available from JEOL) in a condition of 200 kV. The mean particle size and the particle size distribution can be obtained by measuring the particles dispersed in water by dynamic light scattering (particle size distribution measurement apparatus/Nanotrack WAVE). The BET specific surface area of the particles can also be calculated by a nitrogen adsorption method, and the size of the pore and the size of the pores connecting with the mesopore can also be calculated by BJH method (Surface area measuring apparatus commercially available from Microtrac BEL Corp., BELSORP-max).

<Resin Composition>

The porous metal oxide particles of the present embodiment may be used as they are for various types of applications which will be discussed later, or may further be used as a resin composition containing the porous metal oxide particles and a binder resin. The resin composition will be described below.

<Binder Resin>

The binder resins in the present embodiment means those can provide bindings among the porous metal oxide particles, or those can be mediums for uniformly dispersing the porous metal oxide particles therein.

The type of the binder resin that can be used in the present embodiment is not particularly limited. Examples include a thermosetting resin that can be cured by a heat, a photosetting resin that can be cured by radiation of ray such as ultraviolet, or a thermoplastic resin or a water-soluble resin. Among these, resins having film-formability, such as polyolefin-based, poly(meth)acrylic ester-based, polystyrene-based, polyurethane-based, polyvinyl alcohol-based and polyvinylacetal-based resins are preferable.

Examples of thermosetting resin and photosetting resin include epoxy resins, unsaturated polyester resins, phenolic resins, urea-melamine resins, polyurethane resins, silicone resins, diallyl phthalate resins, thermosetting polyimide resins and the like.

Examples of epoxy resin include various types of epoxy resins such as glycidyl ether type such as bisphenol A type epoxy resin, glycidyl ester type, glycidylamine type, cyclic aliphatic type, novolac type, naphthalene type, dicyclopentadiene type epoxy resins. Examples of unsaturated polyester resin include various types of unsaturated polyester resins such as orthophthalate-based, isophthalate-based, telephthalate-based, alicyclic unsaturated acid-based, aliphatic saturated acid-based, bisphenol-based, halogen-containing acid-based, halogen-containing bisphenol-based unsaturated polyester resins. Examples of phenolic resin include resol type, novolac type phenolic resins.

Examples of thermoplastic resin include polyolefin resins, polyvinyl chloride resins, vinylidene chloride-based resins, polystyrene resins, acrylonitrile-butadiene-styrene copolymer resins, acrylonitrile-styrene copolymer resins, styrene-based block copolymer resins, methacrylic resins, polyvinyl alcohol resins (PVA), polyvinylacetal resins (PVB), polyacetal resins, polyamide resins, polycarbonate resins, modified polyphenylene ether resins, thermoplastic polyester resins, fluororesins, polyphenylene sulfide resins, polysulfone resins, amorphous arylate resins, polyetherimide resins, polyether sulfone resins, polyether ketone resins, liquid crystal polymer resins, polyamide imide resins, thermoplastic polyimide resins, syndio-type polystyrene resins and the like.

Examples of polyolefin resin include polyethylene resins, polypropylene resins, α-olefin copolymer resins, polybutene-1 resins, polymethyl pentene resins, cyclic olefin-based polymer resins, ethylene-vinyl acetate copolymer resins, ethylene-methacrylic acid copolymer resins, ionomers and the like.

Examples of polyamide resin include nylon 6, nylon 66, nylon 11, nylon 12 and the like.

Examples of thermoplastic polyester resin include polyethylene terephthalate resins, polybutylene terephthalate resins, polybutylene succinate resins, polylactic resins and the like.

Examples of fluororesins include polytetrafluoroethylene resins, perfluoro alkoxy alkane resins, perfluoroethylene-propene copolymer resins, ethylene-tetrafluoroethylene copolymer resins, polyvinylidene fluoride resins, polychlorotrifluoroethylene resins, ethylene-chlorotrifluoroethylene copolymer resins, tetrafluoroethylene-perfluorodioxole copolymer resins, polyvinyl fluoride resins and the like.

Examples of water-soluble resin include polyvinyl alcohol (PVA), polyvinylpyrrolidone (PVP), polyethylene glycol (PEG) and derivatives thereof and the like.

Resins having film-formability such as polyolefin-based, poly(meth)acrylic ester-based and polystyrene-based resins are preferably the polymer particles having particle size of from 10 to 300 μm, and are capable of forming transparent coating films at a room temperature or with a heat of not higher than 100 degrees C. after drying.

Among the above-described binder resins, epoxy resins, phenolic resins, polyimide resins, polyolefin resins, water-soluble resins, and the above-described resins having film-formability are preferable, in view of the dispersibility and the versatility of the porous metal oxide particles. One of these binder resins may be employed alone, or two or more of these may also be employed.

Weight average molecular weight of the binder resin is preferably from 200 to 100,000, and is more preferably from 500 to 80,000.

In view of delivering performances such as optical characteristics, dielectric constant characteristics, thermal insulating properties and the like, the content of the binder resin is preferably from 30 to 95% by mass, and is more preferably from 40 to 90% by mass, and the content of the porous metal oxide particles of the present invention is preferably from 70 to 5% by mass, and is more preferably from 60 to 10% by mass.

The method of dispersing the porous metal oxide particles in the binder resin is not particularly limited and known methods are applicable, and specifically for example, the following dispersing methods may be used.

In addition to above, the binder resin may be mixed with a dispersion medium such as an organic solvent or water to prepare an emulsion, and the resultant emulsion may be used.

(1) A method, in which a binder resin (or emulsion thereof) and porous metal oxide particles are melted and kneaded with a kneader, optionally in the presence of a solvent and/or a dispersing agent as required, to obtain a master batch containing the porous metal oxide particles (light weighting filler) dispersed in the binder resin.

Examples of the kneader in this method include a bead mill mixer, a tri-roll mill mixer, a homogenizer mixer, a labo-plastomill mixer and the like.

(2) A method, in which a wet process with an addition of a treatment agent is carried out for the porous metal oxide particles which disperses under water, and then the solvent-substituted porous metal oxide particles organosol is added to and mixed with the binder resin (or emulsion thereof).

Examples of treatment agent include organosilicic compounds (surface treatment agent) typified by the above-described silane coupling agent, or anionic surfactants, cationic surfactants, ampholytic surfactants nonionic surfactants and the like.

<Film, Coating Film>

A film or a coating film can be obtained from the resin composition of the present embodiment. The thermal conductivity of the film or the coating film is preferably equal to or lower than 0.1 W/mK, and is more preferably equal to or lower than 0.05 W/mK. This can improve the thermal insulation efficiency. In addition, the HAZE value when the thickness of the dried film or the dried coating film is 10 μm is preferably equal to or lower than 10%, and is more preferably equal to or lower than 5%. This allows providing the film or the coating film having higher transparency.

The method of preparing the film or the coating film is not particularly limited and known methods are applicable, and specifically for example, the film is formed as follows.

A glass substrate is coated with a paint containing the porous metal oxide particles by using a bar coater while adjusting the coating thickness. This is dried for 1 hour to 24 hours at a temperature of 50 degrees C. to 100 degrees C. in an oven, and then the formed film is torn off from the glass substrate to obtain the porous metal oxide particles-containing film or coating film.

The thermal conductivity of the film or the coating film of the present embodiment can be measured by a laser flash method. In addition, the HAZE value of the film or the coating film of the present embodiment can be measured with NDH4000, which is commercially available from Nippon Denshoku Kogyo, assuming that the thickness of the dried film or the dried coating film is 10 μm. The refractive index of the film can be measured with Abbe's refractometer, and the refractive index of the thin coating film can be measured by an ellipsometer.

<Applications>

The porous metal oxide material of the present embodiment can be used for medicines (DDS: drug delivery system), molecular probes, catalysts, adsorbent materials, sensors, paints, inks and the like.

The resin composition comprising the porous metal oxide material of the present embodiment can be used for low dielectric constant materials such as printed circuit boards, or special paints or inks containing functional molecules.

The films or the coating films obtained from resin compositions of the present embodiment can be used for thermal insulation materials such as thermal insulation films or thermal insulation paints for the window glasses in motor vehicles, housings, buildings and the like, antireflection films for displays or touch panels and the like.

Second Embodiment

According to the present embodiment, a coating material containing the following component (A) and component (B) is presented:

(A) the porous metal oxide particles as described in First Embodiment; and (B) a curable functional group-containing compound.

The present embodiment is to provide a coating material containing the porous metal oxide particle as described in First Embodiment and exhibiting sufficient scratch resistance, and applications thereof.

The coating material of the present embodiment is capable of having the refractive index that is controllable to be lower, and is capable of having a hard coating property according to the characteristics of the binder of the component (B), and therefore the coating material can be used for various types of applications, and the desired characteristics can be effectively produced. For example, the coating film obtained from the coating material of the present embodiment can be arranged on the surface of the image display device to provide enhanced visibility and scratch resistance. Also, the method of producing the porous metal oxide particles used in the present invention exhibits enhanced flexibility of the particle design, and ratio of mesopores (porosity) existing in one particle can be freely changed, so that the refractive index can be suitably adjusted.

More specifically, the coating material of the present embodiment comprises the porous metal oxide particles as described in First Embodiment and the compound that is curable with activated energy beam such as ultraviolet ray or heat, has low refractive index, and is capable of forming the transparent coat layer. The present embodiment will be described as follows.

<Porous Metal Oxide Particle>

The porous metal oxide particles as described in First Embodiment are used for the component (A) in the present embodiment. Also, the method of producing the particles as described in First Embodiment can also be used.

<Coating Material>

The porous metal oxide particles in the component (A) of the present embodiment is mixed with the binder of the component (B) composed of the curable functional group-containing compounds, and the resultant mixture is used as the coating material. Most preferably, an activated energy beam-curable functional group-containing compound or a thermosetting functional group-containing silicon compound is used as the component (B) composed of the curable functional group-containing compounds.

<Activated Energy Beam-Curable Functional Group-Containing Compound>

Examples of the activated energy beam-curable functional group-containing compound specifically include (meth)acrylate compounds and poly(methyl)glycidyl ether compounds.

Descriptions on the (meth)acrylate compounds will be made. Preferable (meth)acrylate compounds are (meth)acryl-based oligomers/monomers having two or more (meth)acryloyloxy groups in one molecule. Having two or more (meth)acryloyl oxy groups in one molecule enables the compound to be cured with activated energy beams such as ultraviolet ray, electron beam and the like to form the coated layer having enhanced scratch resistance.

More specifically, examples of this include triethyleneglycol di(meth)acrylate, polyethyleneglycol di(meth)acrylate, neopentylglycol di(meth)acrylate, 1,6-hexanediol di(meth)acrylate, 1,9-nonanediol di(meth)acrylate, dimethylol-tricyclodecane di(meth)acrylate, trimethylolpropane tri(meth)acrylate, ethylene oxide-modified trimethylolpropane tri(meth)acrylate, pentaerythritol tri(meth)acrylate, pentaerythritol tetra(meth)acrylate, dipentaerythritol hexa(meth)acrylate, bisphenol-A diglycidyl ether (meth)acrylic acid adduct, 1,1,3,3,5,5-hexa((meth)acryloxy) cyclotriphosphozene, 1,1,3,3,5,5-hexa(meth)acryloxy ethyloxy cyclotriphosphozene and the like.

Also, for the purpose of improving the scratch resistance, (meth)acrylate compound having urethane bond is preferably added. Generally, this is obtained by a reaction of diisocyanate with hydroxy (meth)acrylate, and urethane (meth)acrylate oligomers obtained by reaction of a combination of diisocyanate with hydroxy (meth)acrylate is specifically exemplified. Examples of the diisocyanate include propane diisocyanate, hexamethylene diisocyanate, isophorone diisocyanate, methylene bis(cyclohexylisocyanate), trimethyl hexamethylene diisocyanate, tolylene diisocyanate, 4,4-diphenylmethane diisocyanate, xylene diisocyanate, norbornene diisocyanate, methyl norbornene diisocyanate and the like, and examples of hydroxy (meth)acrylate include 2-hydroxyethyl (meth)acrylate, 2-hydroxypropyl acrylate, glycidol methacrylate, pentaerythritol tri(meth)acrylate, pentaerythritol tetra(meth)acrylate, ethylene glycol, polyethylene glycol, polypropylene glycol, polytetramethylene glycol and the like.

Among these, in order to increase the hardness after the cure, this preferably has two or more functional groups and further preferably has three or more functional groups, and the use of pentaerythritol tri(meth)acrylate as hydroxy (meth)acrylate is particularly preferable.

In addition, (meth)acryl-based monomer having one (meth)acryloyl group in one molecule may be blended for the purpose of adjustment of the viscosity or the like. More specifically, examples of this include isoamyl (meth)acrylate, lauryl (meth)acrylate, stearyl (meth)acrylate, butoxyethyl (meth)acrylate, ethoxy-diethyleneglycol (meth)acrylate, methoxy-triethyleneglycol (meth)acrylate, methoxy-polyethyleneglycol (meth)acrylate, methoxydipropyleneglycol (meth)acrylate, methoxydiethyleneglycol (meth)acrylate, phenoxyethyl (meth)acrylate, phenoxy-polyethyleneglycol (meth)acrylate, tetrahydrofurfuryl (meth)acrylate, isobonyl (meth)acrylate, 2-hydroxyethyl (meth)acrylate, 2-hydroxypropyl (meth)acrylate, 2-hydroxy-3-phenoxypropyl (meth)acrylate, (meth)acrylic acid, (meth)acrylate glycidyl, 2-(meth)acryloyloxy ethyl-succinic acid, 2-(meth)acryloyloxyethyl-phthalic acid, isooctyl (meth)acrylate, isomyristyl (meth)acrylate, 2-hydroxybutyl (meth)acrylate, methyl (meth)acrylate, ethyl (meth)acrylate, n-butyl (meth)acrylate, isobutyl (meth)acrylate, cyclohexyl methacrylate, benzyl (meth)acrylate, (meth)acryloyl morpholine, perfluorooctyl (meth)acrylate, trifluoroethyl (meth)acrylate and the like.

In addition, a reactive monomer having several vinyl groups or thiol groups may be added for the purpose of the viscosity control and the curability control.

More specifically, N-vinyl pyrrolidone, N-vinyl carbazole, vinyl acetate, trimethylolpropane bis(2-mercaptoacetate), trimethylolpropane bis(3-mercaptopropionate), pentaerythritol tetrakis(2-mercaptoacetate), pentaerythritol (3-mercaptopropionate) and the like may be used.

In addition, in order to promote the cure with ultraviolet or heat, a photopolymerization initiator or a thermal polymerization initiator may be added.

Commercially available products may generally be used as the photopolymerization initiator, and particular examples thereof may include benzophenone, 2,2-dimethoxy-1,2-diphenylethane-1-one (product of BASF, IRGACURE 651), 1-hydroxy-cyclohexyl-phenyl-ketone (product of BASF, IRGACURE 184), 2-hydroxy-2-methyl-1-phenyl-propane-1-one (product of BASF, DAROCUR 1173: Product of Lamberti, ESACURE KL200), oligo(2-hydroxy-2-methyl-1-phenyl-propane-1-one) (Product of Lamberti, ESACURE KIP150), 1-[4-(2-hydroxyethoxy)-phenyl]-2-hydroxy-2-methyl-1-propane-1-one (product of BASF, IRGACURE 2959), 2-methyl-1(4-(methylthio) phenyl)-2-morpholino propane-1-one (product of BASF, IRGACURE 907), 2-benzyl-2-dimethylamino-1-(4-morpholino phenyl)-butanone-1 (product of BASF, IRGACURE 369), bis(2,4,6-trimethylbenzoyl) phenyl phosphine oxide (product of BASF, IRGACURE 819), bis(2,6-dimethoxybenzoyl)-2,4,4-trimethyl-pentyl phosphine oxide (product of BASF, CGI403), 2,4,6-trimethylbenzoyl-diphenylphosphine oxide (=TMDPO: Product of BASF, LUCIRIN TPO, Product of BASF, DAROCUR TPO), thioxanthone or derivatives thereof and the like, and these may be used alone, or a mixture of two or more thereof may be used. The amount of the additives is desirably within the range of from 0.01 to 10.0 parts by weight with respect to 100 parts by weight of (meth)acrylate compound.

In addition, for the purpose of the photosensitization effect, tertiary amines such as, for example, triethanolamine, ethyl-4-dimethylamino benzoate, isopentyl methylamino benzoate and the like may be added.

Examples of thermal polymerization initiator used herein mainly include peroxides such as benzoyl peroxide (=BPO) or the like and azo compounds such as azobis isobutyl nitrile (=AIBN) or the like.

Poly(methyl)glycidyl ether compounds will be described.

Preferable poly(methyl)glycidyl ether compound is an oligomer/monomer having two or more (methyl)glycidyl ether group in one molecule. Having two or more (methyl) glycidyl ether groups in one molecule enables the compound to be cured with activated energy beams such as ultraviolet ray, electron beam and the like to form the coat layer having enhanced scratch resistance. More specifically, for example, the following compounds are exemplified.

Examples of compound having two (methyl)glycidyl ether groups include ethyleneglycol (methyl)diglycidyl ether, triethylene glycol di(methyl)glycidyl ether, tetraethylene glycol di(methyl)glycidyl ether, polyethylene glycol di(methyl)glycidyl ether, glycerin di(methyl)glycidyl ether, 1,4-butanediol di(methyl)glycidyl ether, 1,6-hexanediol di(methyl)glycidyl ether, neopentylglycol (methyl)glycidyl ether and the like. Further, example of compound having three or more (methyl)glycidyl ether groups include glycerin tri(methyl)glycidyl ether, trimethylolpropane tri(methyl) glycidyl ether, pentaerythritol tri(methyl)glycidyl ether, pentaerythritol tetra(methyl)glycidyl ether, dipentaerythritol hexa(methyl)glycidyl ether, dipentaerythritol penta(methyl) glycidyl ether, dipentaerythritol tetra(methyl)glycidyl ether, carbitol polyglycidyl ether and the like.

In order to promote the cure with ultraviolet or heat, a photopolymerization initiator or a thermal polymerization initiator may be added.

More specifically, the type is not particularly limited any one can be used provided that the compound is capable of initiating cationic polymerization with radiation or heat.

Commercially available products may generally be used as the photocationic polymerization initiator, and particular examples thereof preferably used may include Uvacure1590 and 1591 (all are trade names, and are commercially available from Daicel UCB Co., Ltd.,), ADEKA OPTOMER SP-100, SP-170, SP-172, SP-150, SP-152 (all are trade names, and are commercially available from each Asahi Denka Kogyo Corporation), and RHODORSIL-2074 (trade name, commercially available from Rhodia).

One of these photocationic polymerization initiators may be used alone, or two or more of these photocationic polymerization initiators may also be used. The amount of the additives is desirably within the range of from 0.01 to 10.0 parts by weight with respect to 100 parts by weight of poly(methyl)glycidyl ether compound.

Further, a photocationic polymerization accelerator may be jointly used as required. More specifically, examples of this include 9,10-dimethoxy-2-ethyl-anthracene, 9,10-diethoxy anthracene, 2,4-diethyl thioxanthone and the like.

Further, compounds generating cationic species or Lewis acids by heat such as for example, a thermally latent cationic polymerization initiator, may also be jointly used. More specifically, examples of this include: triphenylsulfonium tetrafluoroborate, triphenylsulfonium hexafluoroantimonate, triphenylsulfonium hexafluoroarsenate, tri(4-methoxyphenyl)sulfonium hexafluoroarsenate, diphenyl(4-phenylthiophenyl)sulfonium hexafluoroarsenate, p-t-butylbenzyl tetrahydro thiophenium hexafluoroantimonate and the like; anilinium salt-type compounds such as: N,N-dimethyl-N-benzyl anilinium hexafluoroantimonate, N,N-dimethyl-N-benzyl anilinium tetrafluoroborate, N,N-dimethyl-N-(4-chlorobenzyl) anilinium hexafluoroantimonate, N,N-dimethyl-N-(1-phenylethyl) anilinium hexafluoroantimonate; pyridinium salt-type compounds such as: N-benzyl-4-dimethylamino pyridinium hexafluoroantimonate, N-benzyl-4-diethylamino pyridinium trifluoromethane sulfonate, N-(4-methoxybenzyl)-4-dimethylamino pyridinium hexafluoroantimonate, N-(4-methoxybenzyl)-4-diethylamino pyridinium hexafluoroantimonate and the like; toluidinium salt-type compounds such as N,N-dimethyl-N-(4-methoxybenzyl) toluidinium hexafluoroantimonate, N,N-diethyl-N-(4-methoxybenzyl) toluidinium hexafluoroantimonate and the like; phosphonium salt-type compounds such as ethyl triphenylphosphonium hexafluoroantimonate, tetrabutyl phosphonium hexafluoroantimonate and the like; iodonium salt-type compounds such as: diphenyliodonium hexafluoroarsenate, di-4-chlorophenyl iodonium hexafluoroarsenate, di-4-bromophenyl iodonium hexafluoroarsenate, di-p-tolyl iodonium hexafluoroarsenate, phenyl(4-methoxyphenyl) iodonium hexafluoroarsenate and the like.

The commercially available thermally latent cationic polymerization initiators include, for example, SAN-AID SI-60L, SAN-AID SI-80L, SAN-AID SI-100L, SAN-AID SI-80, SAN-AID SI-100, SAN-AID SI-145, SAN-AID SI-150, SAN-AID SI-160 (All are trade names and commercially available from Sanshin Chemical Ind. Co., Ltd.) and the like.

The above-described initiators may be used alone, or a combination of two or more thereof may be used. In addition, a heat can be jointly used after the irradiation to further promote the cure.

<Thermosetting Group-Containing Organosilicic Compound>

Examples of thermosetting group-containing organosilicic compounds more specifically includes: 3-glycidoxypropyl trimethoxysilane, 3-glycidoxypropyl methyl dimethoxysilane, 3-glycidoxypropyl dimethyl methoxysilane, 3-glycidoxypropyl triethoxysilane, 3-glycidoxypropyl ethyl diethoxysilane, 3-glycidoxypropyl diethyl ethoxysilane, 3-ethyl-3-{[3-(trimethoxysilyl)propoxy]methyl}oxetane, 3-ethyl-3-{[3-(triethoxysilyl)propoxy]methyl}oxetane and the like.

These compounds can form three-dimensional network structure with a heat, thereby providing increased hard coating property. While these silane compounds may be used as they are, it is more preferable in order to further increase the reactivity to use these compounds after creating the state of silanol (Si—OH) by preliminarily hydrolyzing alkoxysilyl group with an acid catalyst such as aqueous hydrochloric acid or with a basic catalyst such as aqueous ammonia, or after creating siloxane bond (Si—O—Si) by partially condensing silanol group. Examples of preferable metal chelate compounds for promoting the thermal curability include: acetylacetonates; amines; amino acids such as glycine and the like; Lewis acids; metal salts of organic acids and the like, each having central metal atom of Cu (II), Zn (II), Co (II), Ni (II), Be (II), Ce (III), Ta (III), Ti (III), Mn (III), La (III), Cr (III), V (III), Co (III), Fe (III), Al (III), Ce (IV), Zr (IV), V (IV) and the like. Among these, acetylacetonate of Al (III) or Fe (III) are more preferable, in terms of the curing condition and the pot life of the coating solution. The amount thereof is desirably within the range of from 0.01 to 10.0 parts by weight with respect to 100 parts by weight of the thermosetting functional group-containing organosilicic compound. Further, perchloric acids can be jointly used. Examples of preferable perchloric acids include perchloric acid, ammonium perchlorate, magnesium perchlorate and the like.

In addition to these compounds, various types of additives such as an ultraviolet absorbing agent, an antioxidizing agent, a silicone-based surfactant, a silicone oil or the like may be added to the coating material composition depending on the purposes.

Concerning the proportions of the porous metal oxide particles (component (A)) and the curable functional group-containing compound (component (B)), which depend on type of the respective components, the component (A) is preferably equal to or larger than 1 part by weight and equal to or smaller than 60 parts by weight, and is more preferably equal to or larger than 5 parts by weight and equal to or smaller than 50 parts by weight, and is further preferably equal to or larger than 10 parts by weight and equal to or smaller than 40 parts by weight, each based on 100 parts by weight of the sum of (A) and (B). The proportion within the above-described ranges allows easily obtaining the coating film having lower refractive index and enhanced scratch resistance.

The preparation of the coating material may be conducted by a known method and is not particularly limited to any specific method, and an example thereof is as follows. First of all, a desired amount the component is mixed in a light-blocking brown glass container or plastic container and is completely mixed while the hard coating material composition is heated as required (roughly equal to or lower than 50 degrees C.). Further, other components are added as required, and the mixture is sufficiently mixed. Further, sufficient deaeration in the stationary condition is achieved to provide the hard coating material composition. While the mixing is carried out by using a magnetic stirrer or a stirring device, other choice such as a mixer, a shaker or the like may alternatively be adopted, depending upon the amount or the viscosity thereof.

When the solvent is added, the examples of available solvent include methyl alcohol, ethyl alcohol, isopropyl alcohol, dimethylformamide (DMF), N,N'-dimethylacetamide, N-methyl-2-pyrrolidone, 2-methoxyethanol (methyl cellosolve), 2-ethoxyethanol (ethylcellosolve), 2-butoxyethanol (butylcellosolve), polyethylene glycol methyl ether (PEGME), polyethylene glycol methyl ether acetate (PEGMEA), diacetone alcohol (DAA), ethyleneglycol, tetrahydrofuran, dioxane, toluene and the like. The viscosity of the coating solution is controlled for the method of coating to the base material, and is preferably from 0.1 cp to 10000 cp, and is more preferably from 0.5 cp to 500 cp, and is further preferably from 1 cp to 100 cp.

<Formation of Coating Film>

Methods of dipping, spin coating, spraying and the like may be adopted for coating onto a base material.

Mercury lamps of low pressure, high pressure, extra high pressure and the like, chemical lamps, metal halide lamps or the like may be used as the light source required for the photopolymerization. Time duration for the photopolymerization is preferably from 1 second to 10 minutes. The time duration shorter than 1 second results in insufficient photocuring, and the time duration longer than 10 minutes may possibly lead to deteriorations of the coat film and base material to cause coloring, crack or the like. The curing is carried out after the coating on the base material is completed, and the solvent is dried off as required. The drying temperature and time are determined by boiling point of the used solvent. The temperature condition required for the thermal polymerization is generally equal to or higher than 50 degrees C., and is preferably equal to or higher than 80 degrees C., and is further preferably equal to or higher than 100 degrees C., while the temperature is determined according to the boiling point of the solvent used, the thermal resistant temperature of the base material, and the type of thermal polymerization initiator.

While the characteristics of the coating film after the cure are not particularly limited, the refractive index in D-line (589.6 nm) of Na is preferably equal to or lower than 1.45, and is more preferably equal to or lower than 1.40.

<Applications>

Low refractive index coat materials of the present embodiment may be used for: image display devices such as a liquid crystal display, a CRT display, a projection display, a plasma display, an electroluminescence display, a reflection screen and the like; coating materials for antireflective film such as a touch panel and the like; and antireflective coatings for spectacle lens and the like.

While preferable embodiments of the present invention have been described above, it is intended to present these embodiments for the purpose of illustrations of the present invention only, and various types of configurations other than those described above may also be adopted.

EXAMPLES

While the present invention will be further specifically described below in reference to Example A and Example B, it is not intended to limit the scope of the present invention to these Examples.

Example A (Synthesis Example of Terminal Branched Polyolefin Based Copolymer)

Number average molecular weight (Mn), weight average molecular weight (Mw) and molecular weight distribution (Mw/Mn) were measured by methods described in the descriptions with a gel permeation chromatography (GPC). In addition, the peak top temperature which was obtained by a measurement with differential scanning calorimetry (DSC) is employed as the melting point (Tm). In addition, while the melting point of polyalkylene glycol moiety was also identified depending on the measurement conditions, this indicates the melting point of polyolefin moiety unless otherwise particularly indicated. In $^1$H-NMR, the polymer was completely dissolved in deuterated-1,1,2,2-tetrachloroethane which was a locking solvent and solvating media in a measurement sample tube, and then the measurement was carried out at 120 degrees C. Concerning chemical shifts, peak of deuterated-1,1,2,2-tetrachloroethane was defined as 5.92 ppm, and then chemical shift values of other peaks were determined. Concerning the particle sizes of particles in the dispersion, 50% mean particle size by volume was measured with Microtrack UPA (commercially available from HONEYWELL). The sample was diluted to 200 folds-500 folds and was negatively stained with phosphotungstic acid, and then the observation of the shape of the particles in the dispersion was carried out with transmission electron microscope (TEM/H-7650 commercially available from Hitachi, Ltd.) under the condition of 100 kV.

(Synthesis Example of Terminal Branched Polyolefin Based Copolymer (T))

Terminal epoxy group-containing ethylene polymer (E) was synthesized according to the following procedures (for example, see Synthesis Example 2 in Japanese Laid-Open Patent Publication No. 2006-131870).

1000 ml of heptane was placed at a room temperature in a stainless-steel autoclave having a capacity of 2000 ml, which was sufficiently substituted with nitrogen, and was heated to 150 degrees C. Successively, the autoclave was pressurized with ethylene to 30 kg/cm$^2$G, and the temperature was maintained. 0.5 ml (0.5 mmol) of hexane solution of MMAO (commercially available from TOSOH FINE CHEM) (aluminum atom conversion 1.00 mmol/ml) was injected with a pressure, and then 0.5 ml (0.0001 mmol) of a toluene solution (0.0002 mmol/ml) of the compound represented by the following general formula (14) was injected with a pressure to initiate the polymerization. The polymerization was carried out under ethylene gas atmosphere at 150 degrees C. for 30 minutes, and then the polymerization was stopped by injecting a small amount of methanol with a pressure. The obtained polymer solution was added in 3 liters of methanol containing a small amount of hydrochloric acid to precipitate polymers. After washing with methanol, this was dried under reduced pressure at 80 degrees C. for 10 hours to obtain ethylene-based polymer having double bond at one terminal (P).

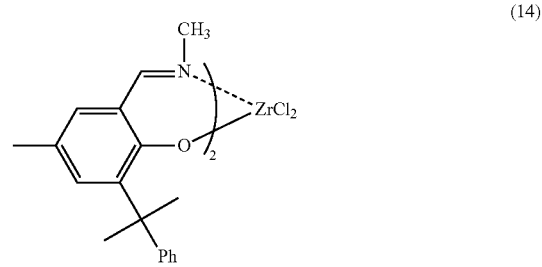

(14)

100 g (vinyl group 108 mmol, assuming Mn is 850) of the above-described ethylene-based polymer having double bond at one terminal (P-1), 300 g of toluene, 0.85 g (2.6 mmol) of Na$_2$WO$_4$, 0.60 g (1.3 mmol) of CH$_3$(nC$_8$H$_{17}$)$_3$NHSO$_4$ and 0.11 g (1.3 mmol) of phosphoric acid were added into a 500 ml separable flask, and was heated to be refluxed while stirring for 30 minutes to completely melt the polymer. After the internal temperature was reached to 90 degrees C., 37 g of 30% hydrogen peroxide water (326 mmol) was dropped for three hours, and then was stirred at the internal temperature of 90-92 degrees C. for 3 hours. Then, 34.4 g (54.4 mmol) of 25% sodium thiosulfate aqueous solution was added thereto while maintaining at 90 degrees C. and was stirred for 30 minutes, and it was found with a peroxide test paper that peroxides in the reaction system was completely decomposed. Then, 200 g of dioxane was added thereto at an internal temperature of 90 degrees C. to crystallize the product, and the resultant solid was collected via filtering, and was washed with dioxane. The obtained solid was stirred in a 50% methanol aqueous solution at room temperature, and then the solid was collected by a filtration and was washed with methanol. The solid was further stirred in 400 g of methanol, and then was collected by a filtration and was washed with methanol.

The resultant product was dried at room temperature under reduced pressure of 1 to 2 hPa to obtain 96.3 g of terminal epoxy group-containing ethylene polymer (E) in a white solid form (yields: 99%, polyolefin conversion ratio: 100%).

The obtained terminal epoxy group-containing ethylene polymer (E) exhibited: Mw=2058, Mn=1118 and Mw/Mn=1.84 (GPC) (terminal epoxide group content: 90 mol %).

$^1$H-NMR: δ (C2D2C14) 0.88 (t, 3H, J=6.92 Hz), 1.18-1.66 (m), 2.38 (dd, 1H, J=2.64, 5.28 Hz), 2.66 (dd, 1H, J=4.29, 5.28 Hz), 2.80-2.87 (m, 1H).

melting point (Tm): 121 degrees C.

84 parts by weight of terminal epoxy group-containing ethylene polymer (E), 39.4 parts by weight of diethanolamine and 150 parts by weight of toluene were put in a 1000 mL flask, and was stirred at 150 degrees C. for 4 hours. Then, acetone was added while cooling to precipitate the reaction product, and a solid substance was collected by filtration. The obtained solid was washed while stirring with acetone aqueous solution for one time and further with acetone for three times, and then a solid was collected by filtration. Then, the resultant product was dried at room temperature under reduced pressure to obtain polymer (I) (Mn=1223, in the following general formula (9), A: a group formed by the polymerization of ethylene (Mn=1075), $R^1$=$R^2$=hydrogen atom, one of $Y^1$ and $Y^2$ is hydroxyl group, and the other is bis(2-hydroxyethyl) amino group).

$^1$H-NMR: δ (C2D2C14) 0.88 (t, 3H, J=6.6 Hz), 0.95-1.92 (m), 2.38-2.85 (m, 6H), 3.54-3.71 (m, 5H).

melting point (Tm): 121 degrees C.

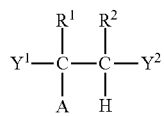

(9)

20.0 parts by weight of polymer (I) and 100 parts by weight of toluene were put in a 500 mL flask equipped with nitrogen supply tubes, a thermometer, cooling tubes and a stirring apparatus, and the heating was carried out in an oil bath of 125 degrees C. while stirring to completely dissolve the solid substance. After being cooled to 90 degrees C., 0.323 parts by weight of 85% KOH, which had preliminarily been dissolved in 5.0 parts by weight of water, was added to the flask, and was mixed under the reflux condition for two hours. Then, water and toluene were distilled off while gradually raising the temperature in the flask to 120 degrees C. Further, the internal pressure of the flask was reduced while supplying a small amount of nitrogen, and internal temperature was further increased to 150 degrees C., and then the conditions were maintained for 4 hours to further distilling water and toluene off from the flask. After being cooled to room temperature, the solid substance solidified in the flask was crushed, and was taken out.

18.0 parts by weight of the obtained solid substance and 200 parts by weight of dehydrated toluene were put in a 1.5 L pressurizing reactor made of stainless steel having a heating unit, a stirrer unit, a thermometer, a pressure gauge, and safety valves, and after the gas phase was replaced with nitrogen, the temperature was increased to 130 degrees C. while stirring. 30 minutes later, 9.0 parts by weight of ethylene oxide was added, and after being maintained at 130 degrees C. for further 5 hours, it was cooled to room temperature to obtain the reactant. The obtained reactant was dried to remove the solvent to obtain terminal branched polyolefin based copolymer (T) (Mn=1835, in general formula (1), A: a group which is formed by polymerization of ethylene (Mn=1075); $R^1$=$R^2$=hydrogen atom; one of $X^1$ and $X^2$ is group represented by general formula (6) ($X^{11}$=polyethylene glycol group) and the other is group represented by general formula (5) (Q=$Q^2$=ethylene group, $X^9$=$X^{10}$=polyethylene glycol group)).

$^1$H-NMR δ (C2D2C14) 0.88 (3H, t, J=6.8 Hz), 1.06-1.50 (m), 2.80-3.20 (m), 3.33-3.72 (m).

melting point (Tm): −16 degrees C. (polyethylene glycol), 116 degrees C.

<Example of Preparing Water Dispersion of Terminal Branched Polyolefin Based Copolymer Particles>
(Preparation of Water Dispersion of 20% by Weight Terminal Branched Polyolefin Based Copolymer (T))

10 parts by weight of (A) terminal branched polyolefin based copolymer (T) obtained in the aforementioned Synthesis Example and 40 parts by weight of distilled water serving as (C) the solvent were placed in a 100 ml autoclave, and after heating and stirring at 140 degrees C. at the speed of 800 rpm for 30 minutes, it was cooled to room temperature while continuing the stirring. 50% mean particle size by volume of the obtained dispersed system was 0.018 μm (10% mean particle size by volume: 0.014 μm, 90% mean particle size by volume: 0.022 μm). The particle sizes of the obtained dispersed system determined from the observation results through the transmission electron microscope were from 0.015 to 0.030 μm.

Example a1

(Synthesis of Porous Silica Particles 1)

1 mL of water dispersion of terminal branched polyolefin based copolymer (T), which was diluted to 1% by weight, and 0.4 mL of 28% ammonia aqueous solution were added in an ethanol/water (10 mL/2.5 mL) mixture liquid, and the resultant was stirred until it became homogeneous. 20 μL of TEOS was added thereto with a micropipette. Then, the resultant was stirred at room temperature for 6 hours. The obtained silica/terminal branched olefin copolymer composite particles were separated and collected by centrifugal separation, and were further washed with ethanol. The obtained powder was dried by using a vacuum dryer. The temperature was elevated from room temperature to 550 degrees C. at a rate of 3.5 degrees C./min., and further, calcination was carried out at 550 degrees C. for 4 hours to remove terminal branched olefin copolymer composite particles to obtain the porous silica particles.

It was found that the porous silica particles were obtained, which had 50% mean particle size by volume of 90 nm and D90/D50 of 1.38 according to the measurements with DLS, and also contained the pores of 10 to 20 nm in the interior thereof according to the TEM observation. The investigations on the pore structure in the nitrogen adsorption process showed that the BET specific surface area was 108 m²/g, and the value calculated using BJH method from the adsorption isothermal curve (BJH pore diameter) was 13 nm and the value calculated using BJH method from the desorption isothermal curve (connecting section) was equal to or lower than 4 nm, and therefore it was found that the three-dimensional cubic phase structure, in which the pores are mutually connected, was created.

In addition to above, in the section A of the present Example, the measurements with DLS were carried out by using a particle size distribution measurement apparatus/nano track WAVE in the condition of being dispersed in water. In addition, silica was used as the porous particles and water was used as the dispersion solvent, and therefore the measurements were carried out by assuming that the refractive index of silica is 1.44 and the refractive index of water is 1.0.

Example a2

(Synthesis of Porous Silica Particles 2)

The porous silica particles were obtained by a method similar to that employed in Synthesis 1, except that the quantity of TEOS was changed to 12.5 μL and the stirring time was for 4 hours.

It was found that the porous silica particles were obtained, which had 50% mean particle size by volume of 70 nm and D90/D50 of 1.32 according to the measurements with DLS, and also contained the pores of 10 to 30 nm in the interior thereof according to the TEM observation. The BET specific surface area was 105 m²/g, and the value calculated using BJH method from the adsorption isothermal curve (BJH pore diameter) was 14 nm and the value calculated using BJH method from the desorption isothermal curve (connecting section) was equal to or lower than 4 nm, and therefore it was found that the three-dimensional cubic phase structure, in which the pores were mutually connected, was created.

Example a3

(Synthesis of Porous Silica Particles 3)

20 mL of water dispersion of 15% by weight of terminal branched polyolefin based copolymer (T) and 5 mL of 28% ammonia aqueous solution were added to 400 mL of ethanol, and the resultant was stirred until it became homogeneous. 3 mL of TEOS was added thereto with a micropipette. Then, the solution was stirred at room temperature for 48 hours. The obtained silica/terminal branched olefin copolymer composite particles were separated and collected by centrifugal separation, and were further washed with ethanol. The obtained powder was dried by using a vacuum dryer. The temperature was elevated from room temperature to 550 degrees C. at a rate of 3.5 degrees C./min., and further, calcination was carried out at 550 degrees C. for 4 hours to remove terminal branched olefin copolymer composite particles to obtain the porous silica particles.

It was found that the porous silica particles were obtained, which had 50% mean particle size by volume of 75 nm and D90/D50 of 1.32 according to the measurements with DLS, and also contained the pores of 10 to 30 nm in the interior thereof according to the TEM observation. The BET specific surface area was 102 m²/g, and the value calculated using BJH method from the adsorption isothermal curve (BJH pore diameter) was 14 nm and the value calculated using BJH method from the desorption isothermal curve (connecting section) was equal to or lower than 4 nm, and therefore it was found that the three-dimensional cubic phase structure, in which the pores were mutually connected, was created.

Example a4

(Synthesis of Porous Silica Particles 4)

40 mL of water dispersion of 15% by weight of terminal branched polyolefin based copolymer (T) and 3 mL of 28% ammonia aqueous solution were added to 150 mL of ethanol, and the mixture liquid was stirred until it became homogeneous. TEOS/ethanol (8.7 mL/35 mL) was added at a time. Then, the resultant was stirred at room temperature for 24 hours. The obtained silica/terminal branched olefin copolymer composite particles were separated and collected by centrifugal separation, and were further washed with ethanol. The obtained powder was dried by using a vacuum dryer. The temperature was elevated from room temperature to 550 degrees C. at a rate of 3.5 degrees C./min., and further, calcination was carried out at 550 degrees C. for 4 hours to remove terminal branched olefin copolymer composite particles to obtain the porous silica particles.

It was found that the porous silica particles were obtained, which had 50% mean particle size by volume of 80 nm and D90/D50 of 1.30 according to the measurements with DLS, and also contained the pores of 10 to 30 nm in the interior thereof according to the TEM observation. The BET specific surface area was 105 m²/g, and the value calculated using BJH method from the adsorption isothermal curve (BJH pore diameter) was 14 nm and the value calculated using BJH method from the desorption isothermal curve (connecting section) was equal to or lower than 4 nm, and therefore it was found that the three-dimensional cubic phase structure, in which the pores were mutually connected, was created.

Example a5

(Synthesis of Porous Silica Particles 5)

72 mL of water dispersion of 15% by weight terminal branched polyolefin based copolymer (T) and 14.4 mL of 28% ammonia aqueous solution were added to 500 mL of ethanol, and the resultant was stirred until it became homogeneous. TEOS/ethanol (36 mL/144 mL) and ethyl triethoxysilane (triethoxy(ethyl)silane)/ethanol (3.6 mL/14.4 mL) were added at a time. Then, the resultant was stirred at room temperature for 4 hours. The obtained silica/terminal branched olefin copolymer composite particles were separated and collected by centrifugal separation, and were further washed with ethanol. The obtained powder was dried by using a vacuum dryer. The temperature was elevated from room temperature to 550 degrees C. at a rate of 3.5 degrees C./min., and further, calcination was carried out at 550 degrees C. for 4 hours to remove terminal branched olefin copolymer composite particles to obtain the porous silica particles.

Figure 3:
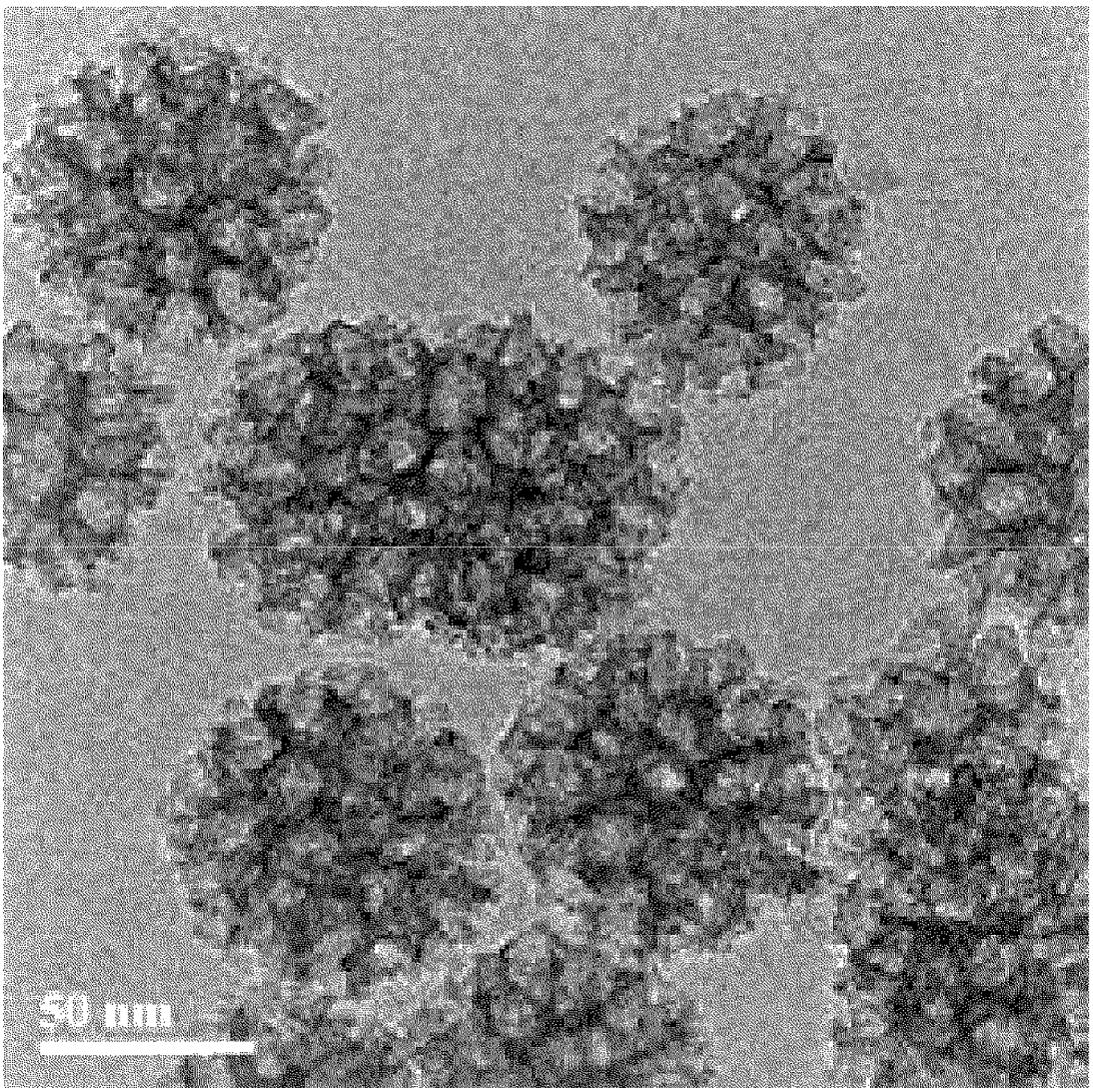
FIG. 3 is a transmission electron microscope (TEM) image of porous silica particles obtained in Example a5.

It was found that the porous silica particles were obtained, which had 50% mean particle size by volume of 80 nm and D90/D50 of 1.32 according to the measurements with DLS, and also contained the pores of 10 to 30 nm in the interior thereof according to the TEM observation (FIG. 3). The BET specific surface area was 194 m²/g, and the value calculated using BJH method from the adsorption isothermal curve (BJH pore diameter) was 11 nm and the value calculated using BJH method from the desorption isothermal curve (connecting section) was equal to or lower than 4 nm, and therefore it was found that the three-dimensional cubic phase structure, in which the pores were mutually connected, was created.

Example a6

(Synthesis of Porous Silica Particles 6)

10.6 mL of ethanol, 1.8 mL of deionized water, 0.8 mL of terminal branched polyolefin based copolymer (T) water dispersion which was prepared to be 15% by weight, and 0.4 mL of 28% ammonia aqueous solution were added to a flask of 50 mL, and the resultant was stirred for 15 minutes. Then, a solution prepared by diluting 1.1 mL of TEOS with 4.4 mL of ethanol was added thereto, and the resultant was stirred at room temperature for 24 hours. The obtained silica/terminal branched olefin copolymer composite particles were separated and collected by centrifugal separation (11000 rpm, 15 minutes), and after being washed with ethanol for 3 times, the product was dried at 80 degrees C. overnight. The temperature was elevated from room temperature to 600 degrees C. in 2 hours, and further, calcination was carried out at 600 degrees C. for 4 hours to remove terminal branched olefin copolymer composite particles to obtain the porous silica particles.

It was found that the porous silica particles were obtained, which had 50% mean particle size by volume of 123 am and D90/D50 of 1.35 according to the measurements with DLS, and also contained the pores of 10 to 20 nm in the interior thereof according to the TEM observation. The investigations on the pore structure in the nitrogen adsorption process showed that the BET specific surface area was 183 m$^2$/g, and the value calculated using BJH method from the adsorption isothermal curve (BJH pore diameter) was 15 nm and the value calculated using BJH method from the desorption isothermal curve (connecting section) was equal to or lower than 4 nm, and therefore it was found that the three-dimensional cubic phase structure, in which the pores were mutually connected, was created.

Example a7

(Synthesis of Porous Silica Particles 7)

9.72 mL of ethanol, 1.8 mL of deionized water, 0.8 mL of terminal branched polyolefin based copolymer (T) water dispersion which was prepared to be 15% by weight, and 0.4 mL of 28% ammonia aqueous solution were added to a flask of 50 mL, and the resultant was stirred for 15 minutes. Then, a solution prepared by diluting 1.32 mL of TEOS with 5.28 mL of ethanol was added thereto, and the resultant was stirred at room temperature for 24 hours.

The obtained silica/terminal branched olefin copolymer composite particles were separated and collected and collect by centrifugal separation (11000 rpm, 15 minutes), and after being washed with ethanol for 3 times, the product was dried at 80 degrees C. overnight. The temperature was elevated from room temperature to 600 degrees C. in 2 hours, and further, calcination was carried out at 600 degrees C. for 4 hours to remove terminal branched olefin copolymer composite particles to obtain the porous silica particles.

It was found that the porous silica particles were obtained, which had 50% mean particle size by volume of 142 nm and D90/D50 of 1.41 according to the measurements with DLS, and also contained the pores of 10 to 20 nm in the interior thereof according to the TEM observation. The investigations on the pore structure in the nitrogen adsorption method showed that the BET specific surface area was 153 m$^2$/g, and the value calculated using BJH method from the adsorption isothermal curve (BJH pore diameter) was 12 nm and the value calculated using BJH method from the desorption isothermal curve (connecting section) was equal to or lower than 4 nm, and therefore it was found that the three-dimensional cubic phase structure, in which the pores were mutually connected, was created.

Example a8

(Synthesis of Porous Silica Particles 8)

The porous silica particles were obtained by a method similar to that employed in Example a6, except that deionized water was 2 mL and water dispersion of the terminal branched polyolefin based copolymer (T) which was prepared to be 15% by weight was 0.6 mL in Example a6.

It was found that the porous silica particles were obtained, which had 50% mean particle size by volume of 242 nm and D90/D50 of 1.74 according to the measurements with DLS, and also contained the pores of 10 to 20 nm in the interior thereof according to the TEM observation. The investigations on the pore structure in the nitrogen adsorption process showed that the BET specific surface area was 102 m$^2$/g, and the value calculated using BJH method from the adsorption isothermal curve (BJH pore diameter) was 14 nm and the value calculated using BJH method from the desorption isothermal curve (connecting section) was equal to or lower than 4 nm, and therefore it was found that the three-dimensional cubic phase structure, in which the pores were mutually connected, was created.

Example a9

(Synthesis of Porous Silica Particles 9)

The porous silica particles were obtained by a method similar to that employed in Example a7, except that deionized water was 2 mL and water dispersion of the terminal branched polyolefin based copolymer (T) which was prepared to be 15% by weight was 0.6 mL in Example a7.

It was found that the porous silica particles were obtained, which had 50% mean particle size by volume of 251 nm and D90/D50 of 1.36 according to the measurements with DLS, and also contained the pores of 10 to 20 nm in the interior thereof according to the TEM observation. The investigations on the pore structure in the nitrogen adsorption process showed that the BET specific surface area was 88 m$^2$/g, and the value calculated using BJH method from the adsorption isothermal curve (BJH pore diameter) was 13 nm and the value calculated using BJH method from the desorption isothermal curve (connecting section) was equal to or lower than 4 nm, and therefore it was found that the three-dimensional cubic phase structure, in which the pores were mutually connected, was created.

Reference Example a1

(Synthesis of Silica Particles)

0.1 mL of 28% aqueous ammonia was added to 5 mL of ethanol and was stirred, and TEOS/ethanol (0.1 mL/0.4 mL) was further added and was stirred for 4 hours. This mixture was dried to obtain the silica particles.

Figure 4:
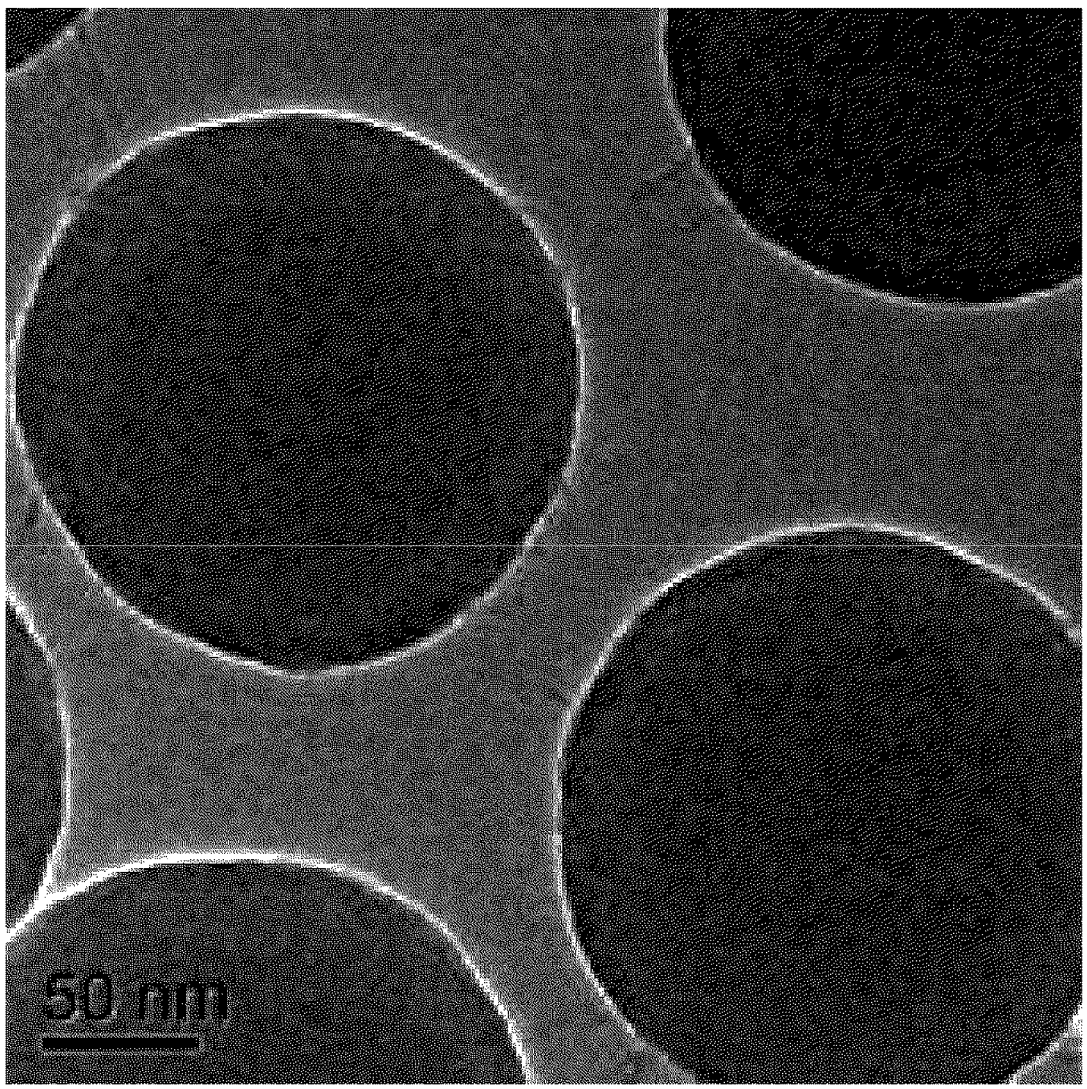
FIG. 4 is a TEM image of silica particles obtained in Reference Example a1.

It was found from the measurements with DLS that the porous silica particles having 50% mean particle size by volume of 150 nm and D90/D50 was 1.2 were obtained. Still, none of pore was confirmed in the interior of the silica particles in the TEM observation (FIG. 4). The BET specific surface area was 20 m$^2$/g.

Comparative Example a1

(Synthesis of Porous Silica Particles 10)

8.2 mg of cationic surfactant CTAB (cetyltrimethylammonium bromide) was dissolved in ethanol/water (10 mL/2 mL), and 0.2 mL of 28% ammonium water was added thereto, and was stirred. 0.1 mL of TEOS was added, and was stirred for 4 hours. The obtained silica/CTAB composite particles were separated and collected by centrifugal separation, and were further washed with ethanol. The obtained powder was dried by using a vacuum dryer. The temperature was elevated from room temperature to 550 degrees C. at a rate of 3.5 degrees C./min., and further, calcination was carried out at 550 degrees C. for 4 hours to remove CTAB to obtain the porous silica particles.

It was found from the measurements with DLS that the porous silica particles having 50% mean particle size by volume of 300 nm and D90/D50 was 1.3 were obtained. In addition, in the present Comparative Example a1, it was difficult to determine the sizes of the pores in the interior of the particles by the TEM observation. In addition, the BET specific surface area was 32 $m^2/g$, and both of the pore sizes obtained in BJH method from the adsorption side and the desorption side were 2 nm. It was estimated that the pore had two-dimensional cylinder structure.

Comparative Example a2

(Synthesis of Porous Silica Particles 11)

The porous silica particles were obtained by a method similar to that employed in Synthesis 10, except that the quantity of CTAB was changed to 10.2 mg.

Figure 5:
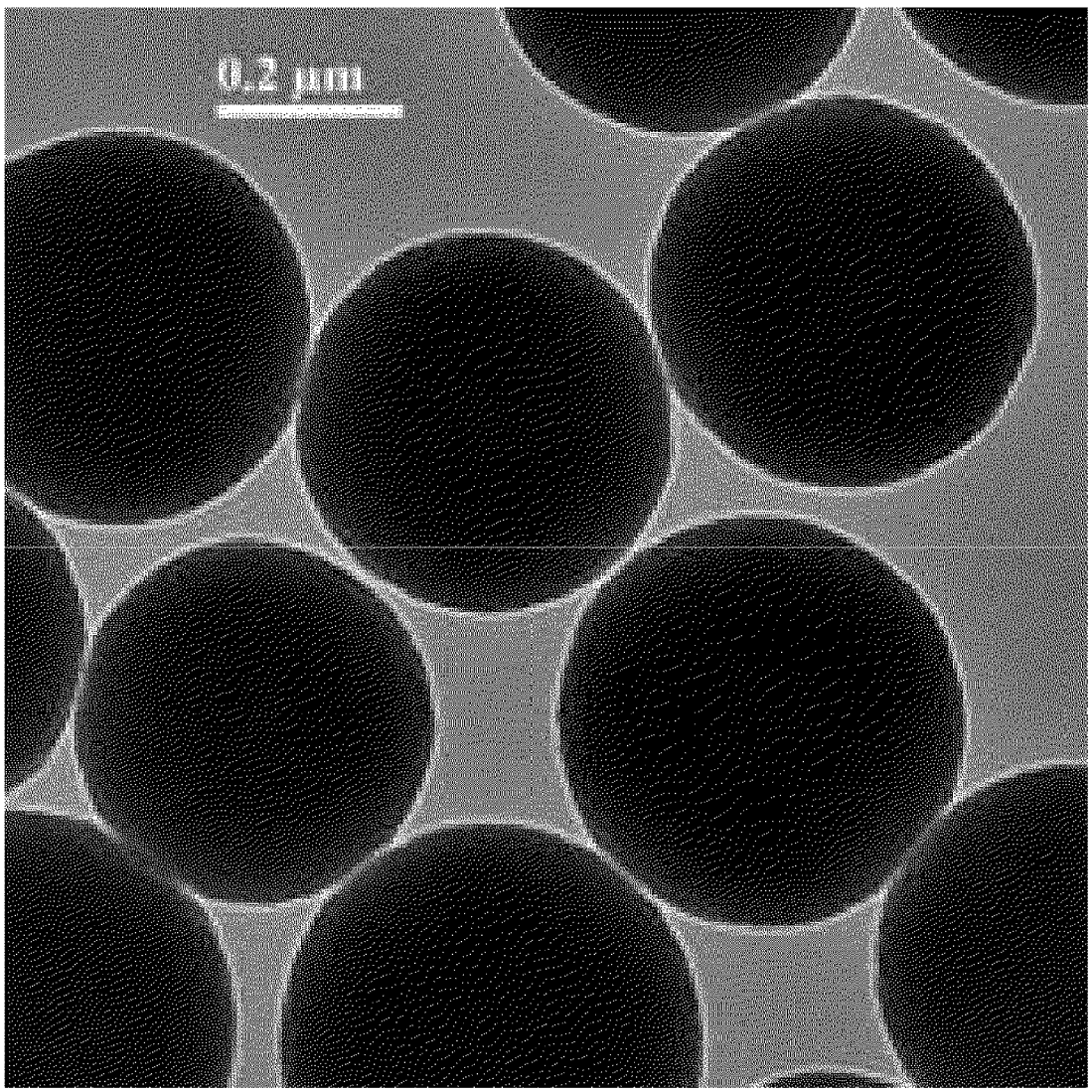
FIG. 5 is a TEM image of porous silica particles obtained in Comparative Example a2.

It was found from the measurements with DLS that the porous silica particles having 50% mean particle size by volume of 410 nm and D90/D50 was 1.3 were obtained. In addition, the results of observing the particles by the TEM are shown in FIG. 5. The BET specific surface area was 64 $m^2/g$, and both of the pore sizes calculated using BJH method from the adsorption side and the desorption side were 2 nm. It was estimated that the pore had two-dimensional cylinder structure.

Comparative Example a3

(Synthesis of Porous Silica Particles 12)

The porous silica particles were obtained by a method similar to that employed in Synthesis 10, except that the quantity of CTAB was changed to 20.5 mg.

Figure 6:
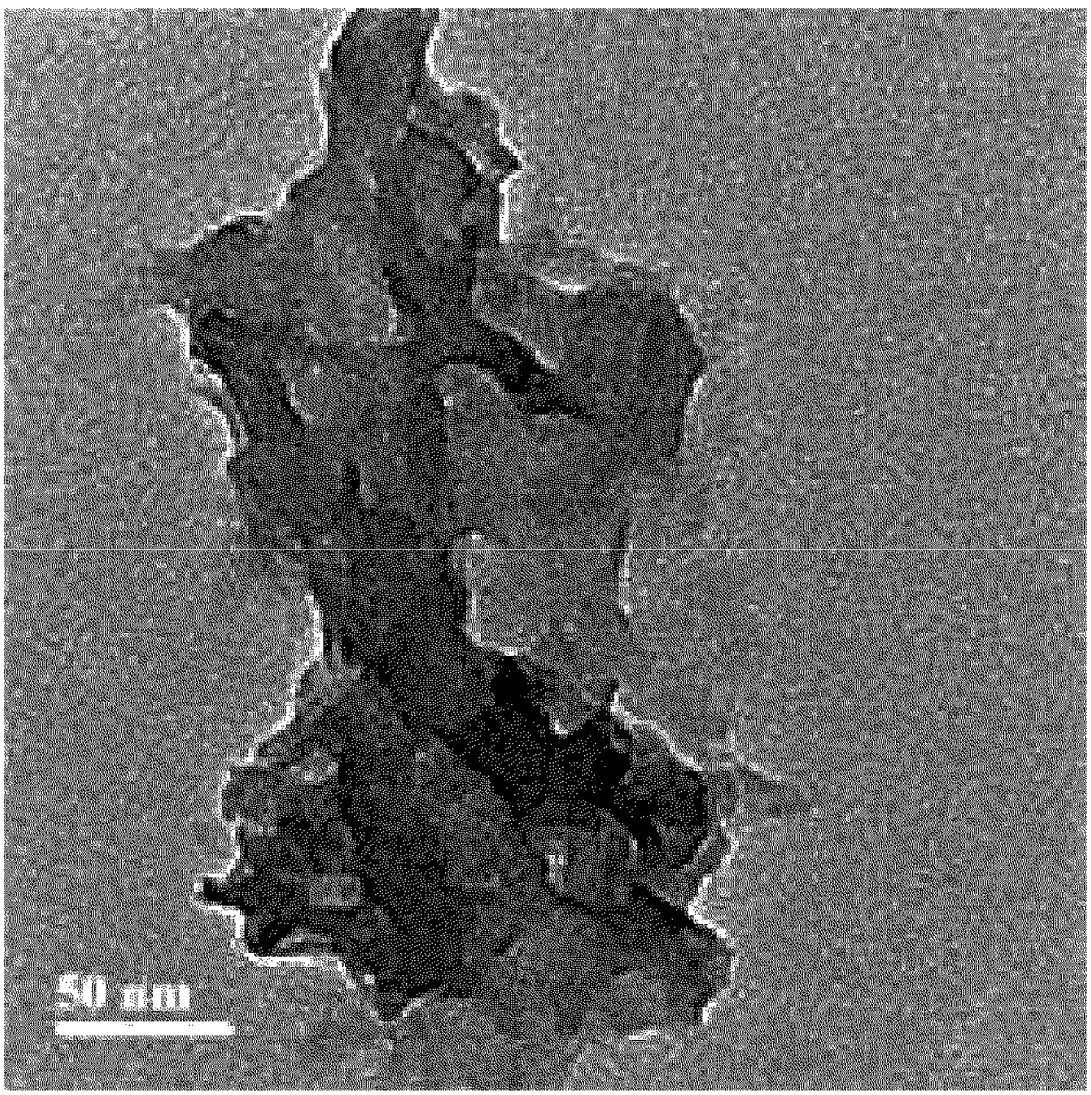
FIG. 6 is a TEM image of porous silica particles obtained in Comparative Example a3.

It was found from the TEM observation that only particles of irregular shapes that are not spherical were obtained (FIG. 6).

Example a10

(Preparation of Water Dispersion of Porous Silica Particles)

Figure 7:
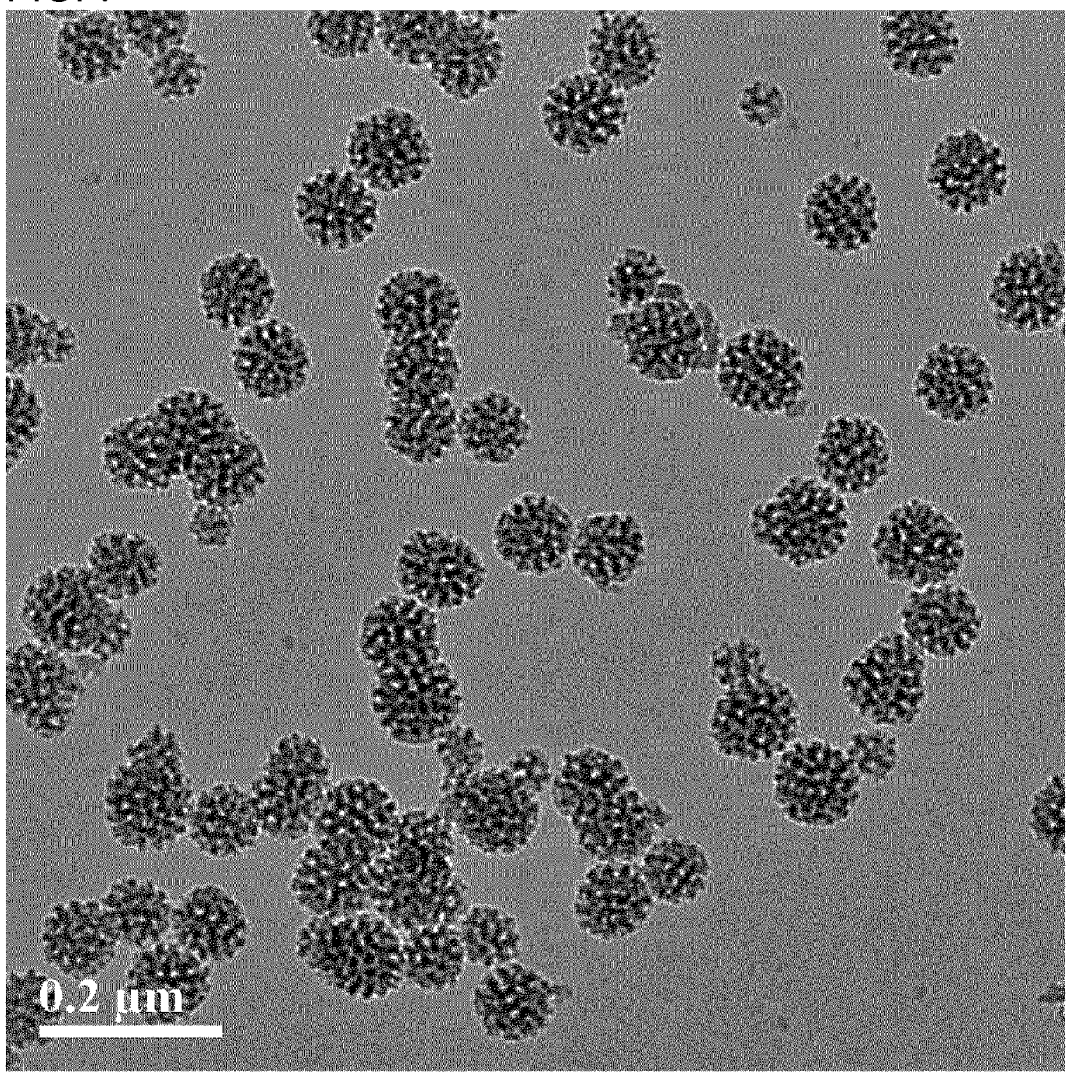
FIG. 7 is a TEM image of porous silica particles in Example a10.
Figure 8:
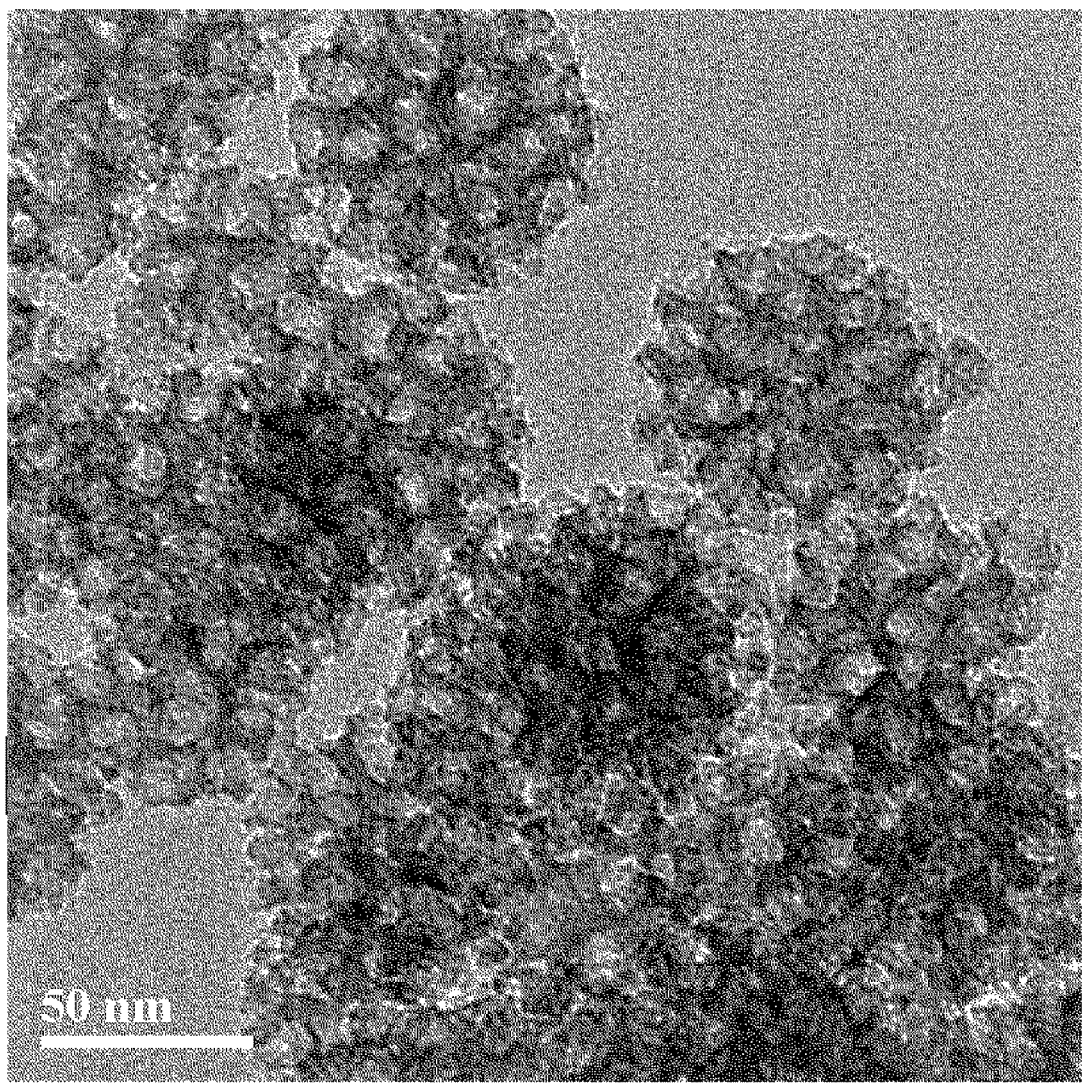
FIG. 8 is TEM image (magnified) of porous silica particles obtained in Example a10.

72 mL of water dispersion of 15% by weight of terminal branched polyolefin based copolymer (T) and 14.4 mL of 28% ammonia water solution were added to 500 mL of ethanol, and the mixture was stirred until it became homogeneous. TEOS/ethanol (36 mL/150 mL) and ethyl triethoxysilane (Triethoxy(ethyl)silane)/ethanol (3.6 mL/14.4 mL) were added at a time. Then, the resultant was stirred at room temperature for 4 hours. The obtained silica/terminal branched olefin copolymer composite particles were separated and collected by centrifugal separation, and were further washed with ethanol. The obtained powder was dried by using a vacuum dryer. The temperature was elevated from room temperature to 450 degrees C. at a rate of 3.5 degrees C./min., and further, calcination was carried out at 550 degrees C. for 4 hours to remove terminal branched olefin copolymer composite particles to obtain the porous silica particles. 10 g of the powder of the porous silica particles were added to 500 mL of water, and the dispersing process was conducted by using a bead mill. After the dispersing process, a homogeneous dispersion without precipitation was obtained. A part of the dispersion was dried, and the TEM observation of the obtained particles was conducted to confirm that the porous structure was maintained (FIG. 7 and FIG. 8).

Figure 9:
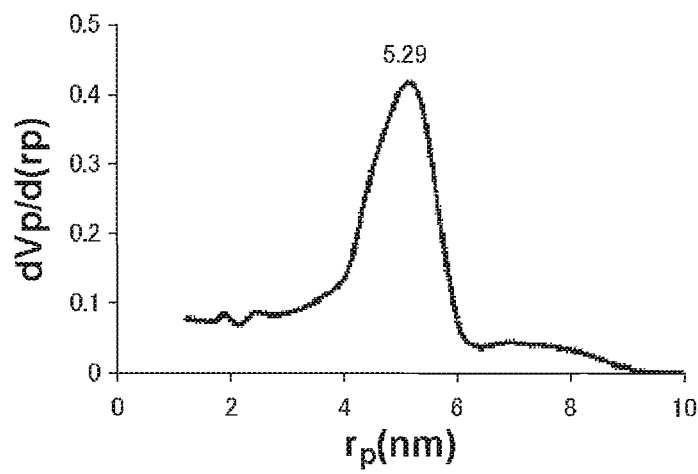
FIG. 9($a$) is a graph, illustrating values of BJH pore size (rp: radius) of a porous silica particle obtained in Example a10 presented by Barrett, Joyner and Halenda (BJH) method from an adsorption isothermal curve of nitrogen adsorption, and FIG. 9($b$) is a graph, illustrating values of connecting pores (rp: radius) between mesopores presented by BJH method from desorption isothermal curve.
Figure 9:
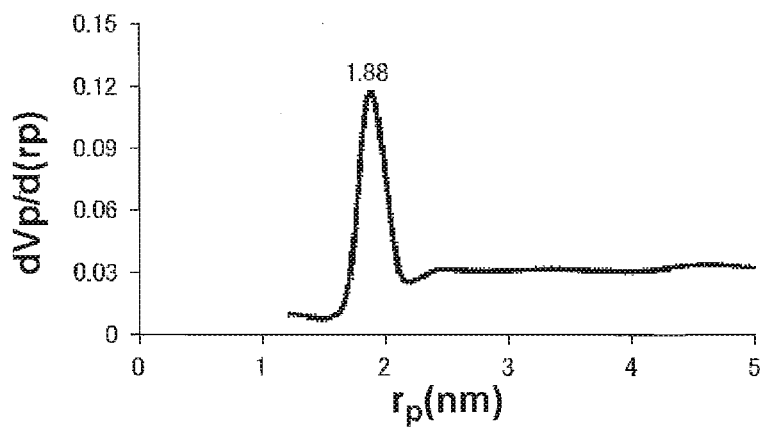

It was found that the porous silica particles were obtained, which had 50% mean particle size by volume of 80 nm and D90/D50 of 1.3 according to the measurements with DLS, and also contained the pores of 10 to 30 nm in the interior thereof according to the TEM observation. In addition, the BET specific surface area was 235 $m^2/g$, and the value calculated using BJH method from the adsorption isothermal curve (BJH pore diameter) was 11 nm and the value calculated using BJH method from the desorption isothermal curve (connecting section) was equal to or lower than 4 nm, and therefore it was found that the three-dimensional cubic phase structure, in which the pores were mutually connected, was created (FIGS. 9(a) and 9(b)).

Example a11

(Preparation of Ethanol Dispersion of Porous Silica Particles)

72 mL of water dispersion of 15% by weight of terminal branched polyolefin based copolymer (T) and 14.4 mL of 28% ammonia water solution were added to 500 mL of ethanol, and the mixture was stirred until it became homogeneous. TEOS/ethanol (36 mL/150 mL) and ethyl triethoxysilane (Triethoxy (ethyl)silane)/ethanol (3.6 mL/14.4 mL) were added thereto at a time. Then, the resultant was stirred at room temperature for 4 hours. The obtained silica/terminal branched olefin copolymer composite particles were separated and collected by centrifugal separation, and were further washed with ethanol. The obtained powder was dried by using a vacuum dryer. The temperature was elevated from room temperature to 450 degrees C. at a rate of 3.5 degrees C./min., and further, calcination was carried out at 550 degrees C. for 4 hours to remove terminal branched olefin copolymer composite particles to obtain the porous silica particles. 10 g of powder of the porous silica particles were added to 437 ml of ethanol, and the dispersing process was conducted by conducting an ultrasonic (US) processing for 30 minutes. After the dispersing process, a homogeneous dispersion without precipitation was obtained. A part of the dispersion was dried, and the TEM observation of the obtained particles was conducted to confirm that the porous structure was maintained.

It was found that the porous silica particles were obtained, which had 50% mean particle size by volume of 80 nm and D90/D50 of 1.3 according to the measurements with DLS, and also contained the pores of 10 to 30 nm in the interior thereof according to the TEM observation. In addition, the BET specific surface area was 235 $m^2/g$, and the value calculated using BJH method from the adsorption isothermal curve (BJH pore diameter) was 11 nm and the value calculated using BJH method from the desorption isothermal curve (connecting section) was equal to or lower than 4 nm, and therefore it was found that the three-dimensional cubic phase structure, in which the pores were mutually connected, was created.

Comparative Example a4

15 parts by weight of methanol serving as a solvent was add to 10 parts by weight of tetramethoxysilane (TMOS), and was stirred at room temperature. 1 part by weight of 1N-hydrochloric acid aqueous solution serving as a catalyst was further dropped therein, and then was stirred at 50 degrees C. for 1 hour to obtain dehydrated condensate of TMOS.

Further 3.4 g of 1N-hydrochloric acid aqueous solution was dropped to the obtained dehydrated condensate of TMOS (for the purpose of adjusting pH after adding terminal branched polyolefin based copolymer to be 3), and the mixture was stirred at room temperature, and 72.4 parts by weight of an aqueous dispersion of terminal branched polyolefin copolymer (T) (solid content 10% by weight) was further dropped, and was stirred at room temperature to prepare a composition of terminal branched polyolefin copolymer/a solution of dehydrated condensate of TMOS. This composition was poured into a spray dryer apparatus at a flow rate of 6 cc/min, and was pressurized (2.6 kg/cm$^2$) at the nozzle outlet temperature of 120 degrees C. and was sprayed to obtain composite fine particles of terminal branched polyolefin based copolymer/silica. The obtained powder was dried by using a vacuum dryer. The temperature was elevated from room temperature to 550 degrees C. at a rate of 3.5 degrees C./min., and further, calcination was carried out at 550 degrees C. for 4 hours to remove terminal branched olefin copolymer composite particles to obtain the porous silica particles.

10 g of the powder of the porous silica particles were added to 500 mL of water, and the dispersing process was conducted by using a bead mill. After the dispersing process, a homogeneous dispersion without precipitation was obtained. A part of the dispersion was dried, and the TEM observation of the obtained particles was conducted to confirm that the porous structure was maintained.

It was found that the porous silica particles were obtained, which had 50% mean particle size by volume of 3.8 μm and D90/D50 of 5.2 according to the measurements with DLS, and also contained the pores of 10 to 30 nm in the interior thereof according to the TEM observation. In addition, the BET specific surface area was 680 m$^2$/g, and the value calculated using BJH method from the adsorption isothermal curve (BJH pore diameter) was 11 nm and the value calculated using BJH method from the desorption isothermal curve (connecting section) was equal to or lower than 4 nm, and therefore it was found that the three-dimensional cubic phase structure, in which the pores were mutually connected, was created.

Example a12

The water dispersion obtained in Example a10 was concentrated to 2.9% by weight via an ultrafiltration process. 8 g of Almatex A9083 (commercially available from Mitsui Chemicals, Inc.; solid concentration: 50% by weight which was aqueous emulsion of an acrylic resin, was mixed to 35 g of this dispersion, and the mixture was poured in a Petri dish, and was dried in an ovens of 70 degrees C. to obtain a uniform and transparent film having a thickness of 50 μm. The HAZE value was 1.7, the refractive index at D-line (589 nm) of the film was 1.38, and the thermal conductivity was 0.04 W/mK.

Example a13

35 g of an ethanol dispersion (2.9% by weight) obtained in Example a11 and a PVB resin ethanol solution (polyvinylbutyral, weight average molecular weight: 50,000-80,000) preliminarily adjusted to 10% were mixed, and the mixture was poured in a Petri dish, and was dried in an ovens of 70 degrees C. to obtain a uniform and transparent film having a thickness of 70 μm. The HAZE value was 0.4, the refractive index at D-line (589 nm) of the film was 1.33, and the thermal conductivity was 0.03 W/mK.

Comparative Example a5

A film was prepared similarly as in Example a12, except that no dispersion was used, to obtain a film made of only the acrylic resin aqueous emulsion Almatex A9083. The HAZE value of this film was 0.3, the refractive index at D-line (589 nm) of the film was 1.47, and the thermal conductivity was 0.58 W/mK.

Comparative Example a6

The porous silica particles obtained in Comparative Example a1 were dispersed with a bead mill similarly as in Example a10, and the resultant dispersion was used to prepare a film by a method similar to that in Example a12. The HAZE value was 12, and the refractive index was impossible to be measured. The thermal conductivity was 0.88 W/mK.

Comparative Example a7

The porous silica particles obtained in Comparative Example a2 were dispersed with a bead mill similarly as in Example a10, and the resultant dispersion was used to prepare a film by a method similar to that in Example a12. The HAZE value was 20, and the refractive index was unmeasurable. The thermal conductivity was 0.92 W/mK.

Comparative Example a8

The porous silica particle dispersion obtained in Comparative Example a4 was used to prepare a film by a method similar to that in Example a12. The HAZE value was 36, and the refractive index was unmeasurable. The thermal conductivity was 0.07 W/mK.

Comparative Example a9

A film was prepared similarly as in Example a13, except that no dispersion was used, to obtain a film made of only PVB. The HAZE value of this film was 0.1, the refractive index at D-line (589 nm) of the film was 1.49, and the thermal conductivity was 0.22 W/mK.

Example B (Synthesis Example of Terminal Branched Polyolefin Based Copolymer)

Number average molecular weight (Mn), weight average molecular weight (Mw) and molecular weight distribution (Mw/Mn) were measured by methods described in the descriptions with a gel permeation chromatography (GPC). In addition, the peak top temperature which was obtained by a measurement with differential scanning calorimetry (DSC) is employed as the melting point (Tm). In addition, while the melting point of polyalkylene glycol moiety was also identified depending on the measurement conditions, this indicates the melting point of polyolefin moiety unless otherwise particularly indicated. In $^1$H-NMR, the polymer was completely dissolved in deuterated-1,1,2,2-tetrachloroethane which was a locking solvent and solvating media in a measurement sample tube, and then the measurement was carried out at 120 degrees C. Concerning chemical shifts, peak of deuterated-1,1,2,2-tetrachloroethane was defined as 5.92 ppm, and then chemical shift values of other peaks were determined. Concerning the particle sizes of particles in the dispersion, 50% mean particle size by volume was measured with Microtrack UPA (commercially available from HONEYWELL). The sample was diluted to 200 folds-500 folds and was negatively stained with phosphotungstic acid, and then the observation of the shape of the particles in the dispersion was carried out with transmission electron microscope (TEM/H-7650 commercially available from Hitachi, Ltd.) under the condition of 100 kV.

(Synthesis Example of Terminal Branched Polyolefin Based Copolymer (T))

Terminal epoxy group-containing ethylene polymer (E) was synthesized according to the following procedures (for example, see Synthesis Example 2 in Japanese Laid-Open Patent Publication No. 2006-131870). 1000 ml of heptane was placed at a room temperature in a stainless-steel autoclave having a capacity of 2000 ml, which was sufficiently substituted with nitrogen, and was heated to 150 degrees C. Successively, the autoclave was pressurized with ethylene to 30 kg/cm$^2$G, and the temperature was maintained. 0.5 ml (0.5 mmol) of hexane solution of MMAO (commercially available from TOSOH FINE CHEM) (1.00 mmol/ml in terms of aluminum atom) was injected with high pressure, and then 0.5 ml (0.0001 mmol) of a toluene solution (0.0002 mmol/ml) of the compound represented by the following general formula (14) was injected with pressure to initiate the polymerization. The polymerization was carried out within ethylene gas atmosphere at 150 degrees C. for 30 minutes, and then the polymerization was stopped by injecting a smaller amount of methanol with high pressure. The obtained polymer solution was added in 3 liters of methanol containing a small amount of hydrochloric acid to precipitate polymers. After washing with methanol, this was dried under reduced pressure at 80 degrees C. for 10 hours to obtain ethylene-based polymer having double bond at one terminal (P).

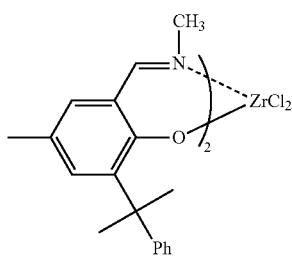

(14)

100 g (vinyl group 108 mmol, assuming Mn is 850) of the above-described ethylene-based polymer having double bond at one terminal (P-1), 300 g of toluene, 0.85 g (2.6 mmol) of Na$_2$WO$_4$, 0.60 g (1.3 mmol) of CH$_3$(nC$^8$H$_{17}$)$_3$NHSO$_4$ and 0.11 g (1.3 mmol) of phosphoric acid were added into a 500 ml separable flask, and was heated to be refluxed while stirring for 30 minutes to completely melt the polymer. After the internal temperature was reached to 90 degrees C., 37 g of 30% hydrogen peroxide water (326 mmol) was dropped for three hours, and then was stirred at the internal temperature of 90-92 degrees C. for 3 hours. Then, 34.4 g (54.4 mmol) of 25% sodium thiosulfate aqueous solution was added thereto while maintaining at 90 degrees C. and was stirred for 30 minutes, and it was found with a peroxide test paper that peroxides in the reaction system was completely decomposed. Then, 200 g of dioxane was added thereto at an internal temperature of 90 degrees C. to crystallize the product, and the resultant solid was collected via filtering, and was washed with dioxane. The obtained solid was stirred in 50% methanol aqueous solution at room temperature, and then the solid was collected by a filtration and was washed with methanol. The solid was further stirred in 400 g of methanol, and then was collected by a filtration and was washed with methanol. The resultant product was dried at room temperature under reduced pressure of 1 to 2 hPa to obtain 96.3 g of terminal epoxy group-containing ethylene polymer (E) in a white solid form (yields: 99%, polyolefin conversion ratio: 100%).

The obtained terminal epoxy group-containing ethylene polymer (E) exhibited: Mw=2058, Mn=1118 and Mw/Mn=1.84 (GPC) (terminal epoxide group content: 90 mol %).

$^1$H-NMR: δ (C2D2C14) 0.88 (t, 3H, J=6.92 Hz), 1.18-1.66 (m), 2.38 (dd, 1H, J=2.64, 5.28 Hz), 2.66 (dd, 1H, J=4.29, 5.28 Hz), 2.80-2.87 (m, 1H).

melting point (Tm): 121 degrees C.

84 parts by weight of terminal epoxy group-containing ethylene polymer (E), 39.4 parts by weight of diethanolamine and 150 parts by weight of toluene were put in a 1000 mL flask, and was stirred at 150 degrees C. for 4 hours. Then, acetone was added while cooling to precipitate the reaction products, and a solid was collected by filtration. The obtained solid was washed while stirring with acetone aqueous solution for one time and further with acetone for three times, and then a solid was collected by filtration. Then, the resultant product was dried at room temperature under reduced pressure to obtain polymer (I) (Mn=1223, A in the following general formula (9): functional group formed by the polymerization of ethylene (Mn=1075), R$^1$=R$^2$=hydrogen atom, one of Y$^1$ and Y$^2$ is hydroxyl group, and the other is bis(2-hydroxyethyl) amino group).

$^1$H-NMR: δ (C2D2C14) 0.88 (t, 3H, J=6.6 Hz), 0.95-1.92 (m), 2.38-2.85 (m, 6H), 3.54-3.71 (m, 5H).

melting point (Tm): 121 degrees C.

(9)

20.0 parts by weight of polymer (I) and 100 parts by weight of toluene were put in a 500 mL flask equipped with nitrogen supply tubes, a thermometer, cooling tubes and a stirring apparatus, and the heating was carried out in an oil bath of 125 degrees C. while stirring to completely dissolve the solid. After being cooled to 90 degrees C., 0.323 parts by weight of 85% KOH, which had preliminarily been dissolved in 5.0 parts by weight of water, was added to the flask, and was mixed under the reflux condition for two hours. Then, water and toluene were distilled off while gradually raising the temperature in the flask to 120 degrees C. Further, the internal pressure of the flask was reduced while supplying a small amount of nitrogen, and internal temperature was further increased to 150 degrees C., and then the conditions were maintained for 4 hours to further distilling water and toluene off from the flask. After being cooled to room temperature, the solid substance solidified in the flask was crushed, and was taken out.

18.0 parts by weight of the obtained solid substance and 200 parts by weight of dehydrated toluene were put in a 1.5 L pressure reactor made of stainless steel having a heating unit, a stirrer unit, a thermometer, a pressure gauge, and safety valves, and after the gas phase was replaced with nitrogen, the temperature was increased to 130 degrees C. while stirring. 30 minutes later, 9.0 parts by weight of ethylene oxide was added, and after being maintained at 130 degrees C. for further 5 hours, it was cooled to room temperature to obtain the reactant. The obtained reactant was dried to remove the solvent to obtain terminal branched polyolefin based copolymer (T) (Mn=1835, in general formula (1), A: group which is formed by polymerization of ethylene (Mn=1075); $R^1=R^2$=hydrogen atom; one of $X^1$ and $X^2$ is group represented by general formula (6) ($X^{11}$=polyethylene glycol group) and the other is group represented by general formula (5) ($Q^1=Q^2$=ethylene group, $X^9=X^{10}$=polyethylene glycol group)).

$^1$H-NMR δ (C2D2C14) 0.88 (3H, t, J=6.8 Hz), 1.06-1.50 (m), 2.80-3.20 (m), 3.33-3.72 (m).

melting point (Tm): −16 degrees C. (polyethylene glycol), 116 degrees C.

<Example of Preparing Water Dispersion of Terminal Branched Polyolefin Based Copolymer Particles>
(Preparation of Water Dispersion of 20% by weight of Terminal Branched Polyolefin Based Copolymer (T))

10 parts by weight of (A) terminal branched polyolefin based copolymer (T) obtained in the aforementioned Synthesis Example and 40 parts by weight of distilled water serving as (C) the solvent were placed in a 100 ml autoclave, and after heating and stirring at 140 degrees C. at the speed of 800 rpm for 30 minutes, it was cooled to room temperature while continuing the stirring. 50% mean particle size by volume of the obtained dispersed system was 0.018 μm (10% mean particle size by volume: 0.014 μm, 90% mean particle size by volume: 0.022 μm). The particle sizes of the obtained dispersed system determined from the observation results through the transmission electron microscope were from 0.015 to 0.030 μm.

<Example of Preparing Porous Silica Particle Dispersion>
(Preparation Example b1 of Diacetone Alcohol Dispersion of Porous Silica Particles)

72 mL of water dispersion of 15% by weight terminal branched polyolefin based copolymer (T) and 14.4 mL of 28% ammonia aqueous solution were added to 500 mL of ethanol, and the mixture was stirred until it became homogeneous. TEOS/ethanol (36 mL/150 mL) and ethyl triethoxysilane (Triethoxy (ethyl)silane)/ethanol (3.6 mL/14.4 mL) were added thereto at a time. Then, the resultant was stirred at room temperature for 4 hours. The obtained silica/terminal branched olefin copolymer composite particles were separated and collected by centrifugal separation, and were further washed with ethanol. The obtained powder was dried by using a vacuum dryer. The temperature was elevated from room temperature to 450 degrees C. at a rate of 3.5 degrees C./min., and further, calcination was carried out at 550 degrees C. for 4 hours to remove terminal branched olefin copolymer composite particles to obtain the porous silica particles. 10 g of powder of the porous silica particles were added to 437 ml of diacetone alcohol, and the dispersing process was conducted by conducting an ultrasonic (US) processing for 30 minutes. After the dispersing process, a homogeneous dispersion without precipitation was obtained. A part of the dispersion was dried, and the TEM observation of the obtained particles was conducted to confirm that the porous structure was maintained.

It was found that the porous silica particles were obtained, which had 50% mean particle size by volume of 80 nm and D90/D50 of 1.3 according to the measurements with DLS, and also contained the pores of 10 to 30 nm in the interior thereof according to the TEM observation. In addition, the BET specific surface area was 235 m$^2$/g, and the value calculated using BJH method from the adsorption isothermal curve (BJH pore diameter) was 11 nm and the value calculated using BJH method from the desorption isothermal curve (connecting section) was equal to or lower than 4 nm, and therefore it was found that the three-dimensional cubic phase structure, in which the pores were mutually connected, was created.

In addition to above, in the section B of the present Example, the obtained porous silica particles were dispersed to water and a particle size distribution measurement apparatus/nanotrack WAVE was used to carry out the measurements with DLS. In addition, silica was used as the porous particles and water was used as the dispersion solvent, and therefore the measurements were carried out by assuming that the refractive index of silica is 1.44 and the refractive index of water is 1.0.

(Preparation Example b2 of Diacetone Alcohol Dispersion of Porous Silica Particles)

4.1 g of cationic surfactant CTAB (cetyltrimethylammonium bromide) was dissolved in ethanol/water (5 L/1 L), and 100 mL of 28% ammonium water was added thereto, and was stirred. 50 mL of TEOS was added, and was stirred for 4 hours. The obtained silica/CTAB composite particles were separated and collected by centrifugal separation, and were further washed with ethanol. The obtained powder was dried by using a vacuum dryer. The temperature was elevated from room temperature to 550 degrees C. at a rate of 3.5 degrees C./min., and further, calcination was carried out at 550 degrees C. for 4 hours to remove CTAB to obtain the porous silica particles. 10 g of powder of the porous silica particles were added to 437 ml of diacetone alcohol, and the dispersing process was conducted by conducting an ultrasonic (US) processing for 30 minutes. After the dispersing process, a homogeneous dispersion without precipitation was obtained.

It was found from the measurements with DLS that the porous silica particles having 50% mean particle size by volume of 300 nm and D90/D50 was 1.3 were obtained. In addition, it was difficult to determine the sizes of the pores in the interior thereof from the TEM observation. In addition, the BET specific surface area was 32 m$^2$/g, and both of the pore sizes obtained in BJH method from the adsorption side and the desorption side were 2 nm. It was estimated that the pore had two-dimensional cylinder structure.

Example b1

20 g of the diacetone alcohol dispersion of the porous silica particles of Preparation Example b1, which was concentrated to 10% by weight, 3.0 g of trimethylolpropane triacrylate, and 1.0 g of pentaerythritol triacrylate hexamethylene diisocyanate urethane prepolymer (commercially available from Kyoeisha Chemical Co., Ltd.: Trade name UA-306H) were mixed, and then 3 g of polyethylene glycol methyl ether was added thereto. Further, 0.15 g of 2,4,6-trimethylbenzoyl diphenyl phosphine oxide serving as a photoinitiator and 0.01 g of a Si-based surfactant (commercially available from Nippon Unicar Co., Ltd.: Trade name FZ-2110) were add thereto, and the mixture was sufficiently stirred to prepare a composition for coating. The prepared composition for coating was used to coat surfaces of a Si-wafer and a silica glass, and the surfaces were irradiated with a high pressure mercury lamp (power 100 W/cm) for 60 seconds to form coating films. The results of the evaluations were shown in Table 1.

In addition to above, the following evaluations were conducted for the coating films having thicknesses of 1.0 to 3.0 μm formed on the Si-wafer or on the silica glass by the spin coating process.

(1) Refractive Index

The refractive index of the coating material of the present embodiment was determined for the film formed on the Si-wafer with an Abbe's refractometer commercially available from ATAGO CO., LTD.

(2) Transparency

As for the transparency of the present embodiment, the transmittance of the film formed on the silica glass was measured from wavelength 400 nm to 600 nm with a film transmissometer (UV2200 commercially available from Shimadzu Corporation).
A: Transmittance was equal to or higher than 90% from 400 nm to 600 nm.
B: Transmittance was equal to or higher than 80% and lower than 90% from 400 nm to 600 nm.
C: Transmittance was lower than 80% from 400 nm to 600 nm.

(3) Scratch Resistance Test

The scratch resistance of the present embodiment was determined for a sample formed on the silica glass, in which the surface was rubbed for 10 reciprocations with a load of 1000 g and 500 g exerted with a #0000 steel wool (commercially available from Nippon Steel Wool Co., Ltd.), and the level of the scratch was estimated by visual observation with the following criteria.
A: No scratch in the area rubbed with 500 g load.
B: 1 to 9 scratches in the area rubbed with 500 g load.
C: 1.0 to 30 scratches in the area rubbed with 500 g load.
D: countless (more than 30) scratches in the area rubbed with 500 g load.

Example b2

20 g of the diacetone alcohol dispersion of the porous silica particles of Preparation Example b1, which was concentrated to 10% by weight, 1.0 g of 1,6-hexanediol diglycidyl ether and 3.0 g of pentaerythritol tri glycidyl ether were mixed, and then 3 g of polyethylene glycol methyl ether was added thereto. Further, 0.15 g of ADEKA OPTOMER-SP-150 serving as a photoinitiator and 0.01 g of a Si-based surfactant (commercially available from Nippon Unicar Co., Ltd.: Trade name FZ-2110) were added thereto, and the mixture was sufficiently stirred to prepare a composition for coating. The prepared composition for coating was used to coat surfaces of a Si-wafer and a silica glass, and the surfaces were irradiated with a high pressure mercury lamp (power 100 W/cm) for 60 seconds to form coating films. The results of the evaluations were shown in Table 1.

Example b3

20 g of the diacetone alcohol dispersion of the porous silica particles of Preparation Example b1, which was concentrated to 10% by weight, 4.2 g of 3-glycidoxypropyltrimethoxysilane serving as a silane compound and/or a compound created by partially condensing thereof, and 1.3 g of 0.1 N hydrochloric acid water were added while stirring, and were further stirred for 2 hours. 7 g of polyethylene glycol methyl ether was added and was sufficiently stirred, and then 0.2 g of Al (III) acetylacetonate serving as a metal chelate compound and 0.01 g of polyether-modified polydimethyl siloxane BYK333 (product name, commercially available from BYK-Chemie GmbH.) serving as a compound having dimethylsiloxane skeleton were added thereto, and after being stirred for 4 hours, the mixture was matured for all night and all day to prepare the composition for hard coating agent. The prepared composition for coating was used to coat surfaces of a Si-wafer and a silica glass, and calcination was carried out at 120 degrees C. for 120 minutes to form the coating film. The results of the evaluations were shown in Table 1.

Comparative Example b1

The coating film was formed by a method similar to that in Example b3, except that 20 g of the diacetone alcohol dispersion of the porous silica particles of Preparation Example b2, which was concentrated to 10% by weight was added instead of the diacetone alcohol dispersion of the porous silica particles of Preparation Example b1. The results of the evaluations were shown in Table 1.

In addition to above, since the coating film obtained by Comparative Example b1 had low film transparency, the refractive index was not able to be precisely measured.

Comparative Example b2

The coating film was formed by a method similar to that in Example b1, except that non-porous silica particles (commercially available from Nissan Chemical Industries, Ltd., Organosilicasol, 70-100 nm ZL Type) were used. The results of the evaluations were shown in Table 1.

Comparative Example b3

The coating film was formed by a method similar to that in Example b2, except that silica particles that were not porous (commercially available from Nissan Chemical Industries, Ltd., Organosilicasol, 70-100 nm ZL Type) were employed. The results of the evaluations were shown in Table 1.

Comparative Example b4

The coating film was formed by a method similar to that in Example b3, except that silica particles that were not porous (commercially available from Nissan Chemical Industries, Ltd., Organosilicasol, 70-100 nm ZL Type) were employed. The results of the evaluations were shown in Table 1.

Comparative Example b5

The coating film was formed by a method similar to that in Example b1, except that none of porous silica particle was added. The results of the evaluations were shown in Table 1.

Comparative Example b6

The coating film was formed by a method similar to that in Example b2, except that none of porous silica particle was added. The results of the evaluations were shown in Table 1.

Comparative Example b7

The coating film was formed by a method similar to that in Example b3, except that none of porous silica particle was added. The results of the evaluations were shown in Table 1.

TABLE 1

|  | Refractive Index | Transparency | Scratch Resistance |
|---|---|---|---|
| Example b1 | 1.36 | A | A |
| Example b2 | 1.34 | A | A |
| Example b3 | 1.31 | A | A |
| Comparative Example b1 | unmeasurable | C | B |
| Comparative Example b2 | 1.50 | A | A |
| Comparative Example b3 | 1.49 | A | A |
| Comparative Example b4 | 1.48 | A | A |
| Comparative Example b5 | 1.51 | A | C |
| Comparative Example b6 | 1.49 | A | C |
| Comparative Example b7 | 1.50 | A | B |

As can be seen from the results of Table 1, the coating films obtained in Examples b1 to b3 exhibited enhanced performances in any evaluation items of the refractive index, the transparency and the scratch resistance.

INDUSTRIAL APPLICABILITY

As described above, since the porous metal oxide materials obtained in the present invention have small particle sizes, and also have mesopores having pore size of equal to or larger than 5 nm, pore structure of which is an ordered three-dimensional cubic phase structure, a mixture thereof with a resin exhibits high transparency, so that the porous metal oxide materials is applicable to optical materials, low dielectric constant materials and thermal insulation materials, and in addition, the particles themselves are expected as materials that can be newly applicable to medicines (DDS: drug delivery system), molecular probes, catalysts, adsorbent materials, sensors, paints, inks and the like.

In addition, since the coating material obtained in the present invention is capable of controlling the refractive index of the obtained coating film to be low, and is capable of having a hard coating property according to the characteristics of the binder, the coating material can be used for: image display devices such as a liquid crystal display, a CRT display, a projection display, a plasma display, an electroluminescence display, a reflection screen and the like; coating materials for antireflective film such as a touch panel and the like; and antireflective coatings for spectacle lens and the like.

The present application claims the benefit of priority based on Japanese Patent Application No. 2013-107963 filed May 22, 2013 and Japanese Patent Application No. 2013-213548 filed Oct. 11, 2013, the entire disclosures thereof are hereby incorporated by reference.

The invention claimed is:

1. Porous metal oxide particles,
the 50% mean particle size by volume thereof being equal to or larger than 50 nm and equal to or smaller than 90 nm,
the ratio of 90% mean particle size by volume to 50% mean particle size by volume (D90/D50) being equal to or lower than 2.0,
the particles having mesopores having a pore size determined by BJH method equal to or larger than 5 nm and equal to or smaller than 30 nm, and
the structure of the pores being a three-dimensional cubic phase structure.

2. The porous metal oxide particles according to claim 1, wherein the 50% mean particle size by volume thereof is equal to or larger than 50 nm and equal to or smaller than 90 nm,
the ratio of 90% mean particle size by volume to 50% mean particle size by volume (D90/D50) is equal to or lower than 1.5,
the particles have mesopores having a pore size determined by BJH method equal to or larger than 5 nm and equal to or smaller than 30 nm, and
the structure of the pores is a three-dimensional cubic phase structure.

3. A method of producing the porous metal oxide particles according to claim 1, comprising:
a step of obtaining a mixture comprising water and/or an organic solvent miscible or partially miscible with water, water-insoluble polymer particles having 50% mean particle size by volume equal to or larger than 5 nm and equal to or smaller than 30 nm, and a base catalyst;
a step of obtaining organic and inorganic composite particles by mixing a metal oxide precursor to said mixture and causing a sol-gel reaction of the metal oxide precursor; and
a step of removing said water-insoluble polymer particles from said organic and inorganic composite particles.

4. The method of producing the porous metal oxide particles according to claim 3,
wherein said water-insoluble polymer particles are particles composed of a terminal branched polyolefin based copolymer represented by the following general formula (1), and having number average molecular weight equal to or lower than $2.5 \times 10^4$,

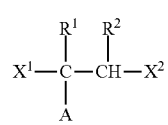
(1)

(In the formula, A represents polyolefin chain, $R^1$ and $R^2$ represent hydrogen atom or alkyl group having 1 to 18 carbon atoms and at least one thereof is hydrogen atom, $X^1$ and $X^2$, which may be the same or different groups, represent a group having straight or branched polyalkylene glycol group).

5. The method of producing the porous metal oxide particles according to claim 4,
wherein $X^2$ and $X^2$ of the terminal branched polyolefin based copolymer represented by said general formula (1) are the same or different groups, and are represented by general formula (2)

$$-E-X^3 \quad (2)$$

(In the formula, E represents oxygen atom or sulfur atom, $X^3$ represents polyalkylene glycol group or group represented by general formula (3)

$$-R^3\text{-}(G)_m \quad (3)$$

(In the formula, $R^3$ represents m+1 valent hydrocarbon group, G, which is the same or different groups, represents a group represented by $-OX^4$ or $-NX^5X^6$ ($X^4$ to $X^6$ represent a polyalkylene glycol group,), m represents a number of bonds of $R^3$ with G and is an integer of from 1 to 10,))
or are represented by general formula (4),

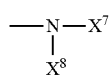

(In the formula, $X^7$ and $X^8$, which are the same or different groups, represent a polyalkylene glycol group or group represented by the above-described general formula (3)).

6. The method of producing the porous metal oxide particles according to claim 4,
wherein said terminal branched polyolefin based copolymer is represented by the following general formula (1a) or general formula (1b),

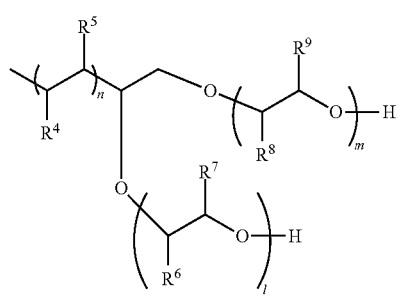 (1a)

(In the formula, $R^4$ and $R^5$ represent hydrogen atom or alkyl group having 1 to 18 carbon atoms and at least one thereof is hydrogen atom, $R^6$ and $R^7$ represent hydrogen atom or methyl group and at least one thereof is hydrogen atom, $R^8$ and $R^9$ represent hydrogen atom or methyl group and at least one thereof is hydrogen atom, l+m represents an integer equal to or larger than 2 and equal to or smaller than 450, n represents an integer equal to or larger than 20 and equal to or smaller than 300,)

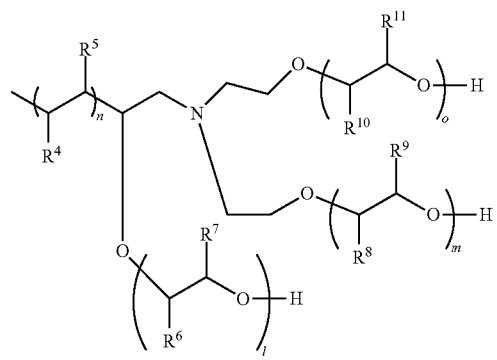 (1b)

(In the formula, $R^4$ and $R^5$ represent hydrogen atom or alkyl group having 1 to 18 carbon atoms and at least one thereof is hydrogen atom, $R^6$ and $R^7$ represent hydrogen atom or methyl group and at least one thereof is hydrogen atom, $R^8$ and $R^9$ represent hydrogen atom or methyl group and at least one thereof is hydrogen atom, $R^{10}$ and $R^{11}$ represent hydrogen atom or methyl group and at least one thereof is hydrogen atom, l+m+o represents an integer equal to or larger than 3 and equal to or smaller than 450, n represents an integer equal to or larger than 20 and equal to or smaller than 300,).

7. The method of producing the porous metal oxide particles according to claim 3,
wherein said step of obtaining a mixture comprises a step of mixing said water and/or said organic solvent capable of dissolving a part or all of water, water dispersion of said water-insoluble polymer particles and said base catalyst.

8. The method of producing the porous metal oxide particles according to claim 3,
wherein the metal oxide precursor is mixed in a condition of being preliminarily diluted with an organic solvent miscible or partially miscible with water in said step of obtaining the organic and inorganic composite particles.

9. A resin composition comprising the porous metal oxide particles according to claim 1 and a binder resin.

10. A film comprising the porous metal oxide particles according to claim 1.

11. A paint comprising the porous metal oxide particles according to claim 1.

12. A thermal insulation material comprising the porous metal oxide particles according to claim 1.

13. A low dielectric constant material comprising the porous metal oxide particles according to claim 1.

14. An ink comprising the porous metal oxide particles according to claim 1.

15. A medicinal agent adapting a drug delivery system (DDS) comprising the porous metal oxide particles according to claim 1, wherein a drug is contained within the mesopores.

16. A coating material comprising a component (A) and a component (B):
(A) the porous metal oxide particles according to claim 1; and
(B) a curable functional group-containing compound.

17. The coating material according to claim 16,
wherein the component (B) is an activated energy beam-curable functional group-containing compound or a thermosetting functional group-containing silicon compound.

18. The coating material according to claim 16,
wherein ratio of the component (A) to 100 parts by weight of the components (A) and (B) in total is equal to or higher than 1 part by weight and equal to or lower than 60 parts by weight.

19. A coating film obtained by curing the coating material according to claim 16.

20. A film comprising the coating film according to claim 19 in a surface section thereof.

21. A lens comprising the coating film according to claim 19 in a surface section thereof.

22. An image display device comprising the coating film according to claim 19 on the surface thereof.

* * * * *